(12) United States Patent
Cragg

(10) Patent No.: US 6,558,386 B1
(45) Date of Patent: May 6, 2003

(54) AXIAL SPINAL IMPLANT AND METHOD AND APPARATUS FOR IMPLANTING AN AXIAL SPINAL IMPLANT WITHIN THE VERTEBRAE OF THE SPINE

(75) Inventor: Andrew H. Cragg, Edina, MN (US)

(73) Assignee: TranS1 Inc., Wilmington, NC (US)

( * ) Notice: Subject to any disclaimer, the term of this patent is extended or adjusted under 35 U.S.C. 154(b) by 218 days.

(21) Appl. No.: 09/684,820

(22) Filed: Oct. 10, 2000

Related U.S. Application Data
(60) Provisional application No. 60/182,748, filed on Feb. 16, 2000.

(51) Int. Cl.[7] ............................................. A61B 17/70
(52) U.S. Cl. ........................................ 606/61; 606/80
(58) Field of Search ............................ 606/60, 61, 72, 606/73, 80; 623/17.11, 17.16

(56) References Cited

U.S. PATENT DOCUMENTS

| | | | |
|---|---|---|---|
| 1,630,239 | A | 5/1927 | Binkley et al. |
| 3,367,326 | A | 2/1968 | Frazier |
| 3,554,192 | A | 1/1971 | Isberner |
| 3,892,232 | A | 7/1975 | Neufeld |
| 4,135,506 | A | 1/1979 | Ulrich |
| 4,170,990 | A | 10/1979 | Baumgart et al. |
| 4,265,231 | A | 5/1981 | Scheller, Jr. et al. |
| 4,401,112 | A | 8/1983 | Rezaian |
| 4,453,539 | A | 6/1984 | Raftopoulos et al. |
| 4,541,423 | A | 9/1985 | Barber |

(List continued on next page.)

FOREIGN PATENT DOCUMENTS

| | | |
|---|---|---|
| EP | 0 611 116 B1 | 4/1994 |
| WO | WO 95/22285 | 8/1995 |
| WO | WO 97/40878 | 11/1997 |
| WO | WO 98/38918 | 9/1998 |
| WO | WO 99/47055 | 9/1999 |
| WO | WO 02/058599 A2 | 8/2000 |
| WO | WO 00/67650 | 11/2000 |
| WO | WO 02/09801 A1 | 2/2002 |
| WO | WO 02/13732 A2 | 2/2002 |
| WO | WO 02/34120 A2 | 5/2002 |

OTHER PUBLICATIONS

J. J. Trambert, MD, "Percutaneous Interventions in the Presacral Space: CT–guided Precoccygeal Approach—Early Experience", *Radiology 1999*; 213:901–904.

R. Johnsson et al., "Posterolateral lumbar fusion using facet joint fixation with biodegradable rods: a pilot study", *Eur Spine J.*, (1997) 6:144–148.

R. P. Louis, MD, "Anatomy, Physiology, and Biomechanics of the Lumbopelvic Junction", *Lumbosacral and Spinopelvic Fusion*, Chapter 1 (pp. 1–11) Lippincott–Raven Pub. (1996).

(List continued on next page.)

*Primary Examiner*—David O. Reip
(74) *Attorney, Agent, or Firm*—Knobbe, Martens, Olson & Bear, LLP

(57) ABSTRACT

Axial spinal implants for fusing and/or stabilizing spinal vertebrae and methods and apparatus for implanting on or more such spinal implants axially within one or more axial bore within vertebral bodies in alignment with a visualized, trans-sacral axial instrumentation/fusion (TASIF) line in a minimally invasive, low trauma manner. Attachment mechanisms are provided that affix or force the preformed axial spinal implants to or against the vertebral bone along the full length of a TASIF axial bore or bores or pilot holes or at the cephalad end and/or caudal end of the TASIF axial bore or bores or pilot holes. The engagement of the vertebral body is either an active engagement upon implantation of the spinal implant into the TASIF bore or a passive engagement of the external surface configuration with the vertebral bone caused by bone growth about the external surface configuration.

17 Claims, 15 Drawing Sheets

U.S. PATENT DOCUMENTS

| | | |
|---|---|---|
| 4,553,273 A | 11/1985 | Wu |
| 4,554,914 A | 11/1985 | Kapp et al. |
| 4,573,448 A | 3/1986 | Kambin |
| 4,636,217 A | 1/1987 | Ogilvie et al. |
| 4,756,649 A | 7/1988 | Heule |
| 4,844,088 A | 7/1989 | Kambin |
| 4,862,891 A | 9/1989 | Smith |
| RE33,258 E | 7/1990 | Onik et al. |
| 4,966,604 A | 10/1990 | Reiss |
| 4,969,888 A | 11/1990 | Scholten et al. |
| 5,002,546 A | 3/1991 | Romano |
| 5,015,255 A | 5/1991 | Kuslich |
| 5,030,201 A | 7/1991 | Palestrant |
| 5,059,193 A | 10/1991 | Kuslich |
| 5,062,850 A | 11/1991 | MacMillan et al. |
| 5,071,437 A | 12/1991 | Steffee |
| 5,171,279 A | 12/1992 | Mathews |
| 5,190,546 A | 3/1993 | Jervis |
| 5,192,326 A | 3/1993 | Bao et al. |
| 5,195,968 A | 3/1993 | Lundquist et al. |
| 5,242,443 A | 9/1993 | Kambin |
| 5,242,444 A | 9/1993 | MacMillan |
| 5,242,461 A | 9/1993 | Kortenbach et al. |
| 5,258,031 A | 11/1993 | Salib et al. |
| 5,269,785 A | 12/1993 | Bonutti |
| 5,285,795 A | 2/1994 | Ryan et al. |
| 5,290,289 A | 3/1994 | Sanders et al. |
| 5,313,962 A | 5/1994 | Obenchain |
| 5,336,223 A | 8/1994 | Rogers |
| 5,357,983 A | 10/1994 | Mathews |
| 5,366,457 A | 11/1994 | McGuire et al. |
| 5,383,884 A | 1/1995 | Summers |
| 5,395,188 A | 3/1995 | Bailey et al. |
| 5,395,317 A | 3/1995 | Kambin |
| 5,396,880 A | 3/1995 | Kagan et al. |
| 5,403,276 A | 4/1995 | Schechter et al. |
| 5,415,661 A | 5/1995 | Holmes |
| 5,433,739 A | 7/1995 | Sluijter et al. |
| 5,480,440 A | 1/1996 | Kambin |
| 5,496,322 A | 3/1996 | Mathews |
| 5,505,732 A | 4/1996 | Michelson |
| 5,514,137 A | 5/1996 | Coutts |
| 5,514,180 A | 5/1996 | Heggeness et al. |
| 5,545,228 A | 8/1996 | Kambin |
| 5,549,679 A | 8/1996 | Kuslich |
| 5,554,163 A | 9/1996 | Shturman |
| 5,558,674 A | 9/1996 | Heggeness et al. |
| 5,562,736 A | 10/1996 | Ray et al. |
| 5,569,248 A | 10/1996 | Mathews |
| 5,571,189 A | 11/1996 | Kuslich |
| 5,571,190 A | 11/1996 | Ulrich et al. |
| 5,584,887 A | 12/1996 | Kambin |
| 5,630,816 A | 5/1997 | Kambin |
| 5,653,708 A | 8/1997 | Howland |
| 5,665,122 A | 9/1997 | Kambin |
| 5,669,909 A | 9/1997 | Zdeblick et al. |
| 5,700,291 A | 12/1997 | Kuslich et al. |
| 5,702,454 A | 12/1997 | Baumgartner |
| 5,702,455 A | 12/1997 | Saggar |
| 5,713,904 A | 2/1998 | Errico et al. |
| 5,728,097 A | 3/1998 | Mathews |
| 5,735,899 A | 4/1998 | Schwartz et al. |
| 5,741,253 A | 4/1998 | Michelson |
| 5,741,261 A | 4/1998 | Moskovitz et al. |
| 5,762,629 A | 6/1998 | Kambin |
| 5,785,709 A | 7/1998 | Kummer et al. |
| 5,792,044 A | 8/1998 | Foley et al. |
| 5,827,328 A | 10/1998 | Buttermann |
| 5,885,292 A | 3/1999 | Moskovitz et al. |
| 5,888,220 A | 3/1999 | Felt et al. |
| 5,888,223 A | 3/1999 | Bray, Jr. |
| 5,891,147 A | 4/1999 | Moskovitz et al. |
| 5,902,231 A | 5/1999 | Foley et al. |
| 5,906,616 A | 5/1999 | Pavlov et al. |
| 5,954,635 A | 9/1999 | Foley et al. |
| 5,964,761 A | 10/1999 | Kambin |
| 5,968,062 A | 10/1999 | Thomas et al. |
| 5,972,015 A | 10/1999 | Scribner et al. |
| 5,976,146 A | 11/1999 | Ogawa et al. |
| 5,976,187 A | 11/1999 | Richelsoph |
| 5,980,604 A | 11/1999 | Sharkey et al. |
| 5,989,256 A | 11/1999 | Kuslich et al. |
| 6,007,487 A | 12/1999 | Foley et al. |
| 6,010,502 A | 1/2000 | Bagby |
| 6,019,792 A | 2/2000 | Cauthen |
| 6,022,362 A | 2/2000 | Lee et al. |
| 6,030,162 A | 2/2000 | Huebner |
| 6,033,406 A | 3/2000 | Mathews |
| 6,053,916 A | 4/2000 | Moore |
| 6,056,749 A | 5/2000 | Kuslich |
| 6,066,152 A | 5/2000 | Strauss et al. |
| 6,066,154 A | 5/2000 | Reiley et al. |
| 6,395,007 B1 | 5/2000 | Bhatnager et al. |
| 6,080,099 A | 6/2000 | Slater et al. |
| 6,086,589 A | 7/2000 | Kuslich et al. |
| 6,093,207 A | 7/2000 | Pisharodi |
| 6,095,149 A | 8/2000 | Sharkey et al. |
| 6,120,502 A | 9/2000 | Michelson |
| 6,123,705 A | 9/2000 | Michelson |
| 6,127,597 A | 10/2000 | Beyar et al. |
| 6,152,871 A | 11/2000 | Foley et al. |
| 6,162,170 A | 12/2000 | Foley et al. |
| 6,175,758 B1 | 1/2001 | Kambin |
| 6,176,823 B1 | 1/2001 | Foley et al. |
| 6,206,822 B1 | 3/2001 | Foley et al. |
| 6,206,826 B1 | 3/2001 | Foley et al. |
| 6,210,412 B1 | 4/2001 | Michelson |
| 6,217,509 B1 | 4/2001 | Foley et al. |
| 6,264,656 B1 | 7/2001 | Michelson |
| 6,315,795 B1 | 11/2001 | Scarborough et al. |
| 6,371,990 B1 | 4/2002 | Ferree |
| 6,379,334 B1 | 4/2002 | Frassica |
| 6,387,130 B1 | 5/2002 | Stone et al. |
| 6,402,750 B1 | 6/2002 | Atkinson et al. |
| 6,447,514 B1 | 9/2002 | Stalcup et al. |
| 6,447,518 B1 | 9/2002 | Krause et al. |
| 2002/0022888 A1 | 2/2002 | Serhan et al. |
| 2002/0032444 A1 | 3/2002 | Mische |
| 2002/0038123 A1 | 3/2002 | Visotsky et al. |
| 2002/0107573 A1 | 8/2002 | Steinberg |

OTHER PUBLICATIONS

M. R. Zindrick, MD et al., "Clinical Anatomy of the Lumbrosacral Junction and Pelvis" *Lumbosacral and Spinopelvic Fusion*, Chapt. 2 (pp. 13–25) Lippincott–Raven Pub. (1996).

J. W. Olgilvie, MD et al., "Overview of Fixation to the Sacrum & Pelvis in Spinal Surgery", *Lumbosacral and Spinopelvic Fusion*, Chapter 17 (pp. 191–198) Lippincott–Raven Pub. (1996).

S. A. Caruso, ME et al., "Instrumented Fusions of the Lumbosacral Spine: A Technical Overview", *Lumbosacral and Spinopelvic Fusion*, Chapter 18 (pp. 199–210) Lippincott–Raven Pub. (1996).

R. P. Louis, MD, "Lumbopelvic Fusion", *Lumbosacral and Spinopelvic Fusion*, Chapter 38 (pp. 479–492) Lippincott–Raven Pub. (1996).

J. Dove, FRCS, "The Hartshill System for the Front of the Lumbosacral Spine", *Lumbosacral and Spinopelvic Fusion*, Chapter 42 (pp. 539–543) Lippincott–Raven Pub. (1996).

P. Kambin, MD et al., "Arthroscopic Fusion of the Lumbosacral Spine", *Lumbosacral and Spinopelvic Fusion*, Chapter 44 (pp. 565–577) Lippincott–Raven Pub. (1996).

B. Jeanneret, et al., "Posterior Stabilization L5–S1 Isthmic Spondylolisthesis with Paralaminar Screw Fixation: Anatomical and Clinical Results," *Journal of Spinal Disorders*, vol. 9, No. 3, pp. 223–233 (1996) Lippincott–Raven Publishers, Philadelphia.

Jason A. Smith, MD, et al., "Clinical Outcome of Trans–Sacral Interbody Fusion After Partial Reduction for High–Grade L5–S1 Spondylolisthesis," *Spine*, 2001, vol. 26, No. 20, pp. 2227–2234.

Michael MacMilland, MD, et al., "Percutaneous Lumbosacral Fixation and Fusion," *Percutaneous Spine Techniques*, Jan. 1996, vol. 7, No. 1, pp. 99–106.

Curtis A. Dickman, M.D., et al., "Transpedicular screw–rod fixation of the lumbar spine: operative technique and outcome in 104 cases," *J. Neurosurg*, Dec., 1992, vol. 77, pp. 860–870.

Richard M. Slone, MD, et al., "Spinal Fixation, Part 1, Basic Hardware, and Fixation Techniques for the Cervical Spine," *RadioGraphics*, 1993, vol. 13, No. 2, pp. 341–356.

Richard M. Slone, MD, et al., "Spinal Fixation, Part 2, Fixation Techniques and Hardware for the Thoracic and Lumbosacral Spine," *RadioGraphics*, 1993, vol. 13, No. 3, pp. 521–543.

Michael MacMillan, et al., "Biomechanical Analysis of a New Anterior Spine Implant for Post–Corpectomy Instability," *Journal of Spinal Disorders*, 1995, vol. 8, No. 1, pp. 56–61.

Hallett H. Mathews, M.D., "Minimally Invasive Fusion Techniques, Percutaneous Interbody Fusions," *Orthopedic Clinics of North America*, Oct. 1998, vol. 29, No. 4.

Parviz Kambin, M.D., et al., "Arthroscopic Microdiscectomy: An Alternative to Open Disc Surgery," *The Mount Sinai Journal of Medicine*, Sep. 2000, vol. 67, No. 4.

Hallett H. Mathews, M.D., et al., "Perspectives on Modern Orthopaedics, Minimally Invasive Techniques for the Treatment of Intervertebral Disk Herniation," *Journal of the American Academy of Orthopaedic Surgeons*, Mar./Apr. 2002, vol. 10, No. 2.

Parviz Kambin, M.D., "Percutaneous Spine Techniques, Diagnostic and Therapeutic Spinal Arthroscopy," *Neurosurgery Clinics of North America*, Jan. 1996, vol. 7, No. 1.

Parviz Kambin, M.D., et al., "Arthroscopic Discectomy of the Lumbar Spine," *Clinical Orthopaedics and Related Research*, Apr. 1997, No. 337.

U.S. patent application Publication No. 2002/0082598 A1, *Percutaneous Vertebral Fusion System*, published Jun. 27, 2002.

U.S. patent application Publication No. 2002/0068939 A1, *Expandable Orthopedic Device*, published Jun. 6, 2002.

John L. Emmett, M.D., M.S. (Urology), David M. Witten, M.D., M.S. (Radiology)—vol. 1, Third Edition—Clinical Urography—An Atlas and Textbook of Roentgenologic Diagnosis—1971—Phneumography (Retroperitoneal Gas [Air] Insufflation; Perirenal Insufflation; Presacral Insufflation).

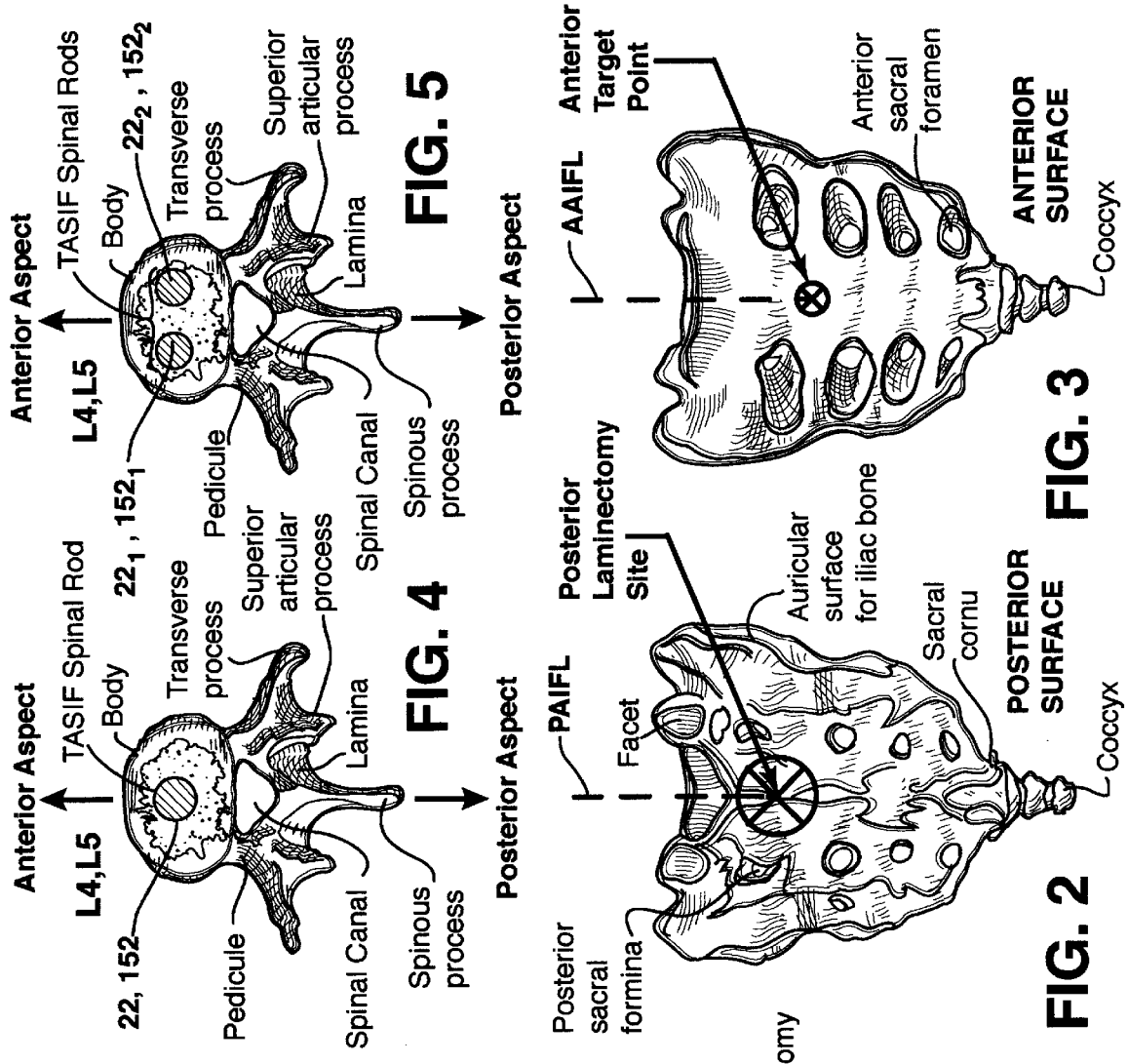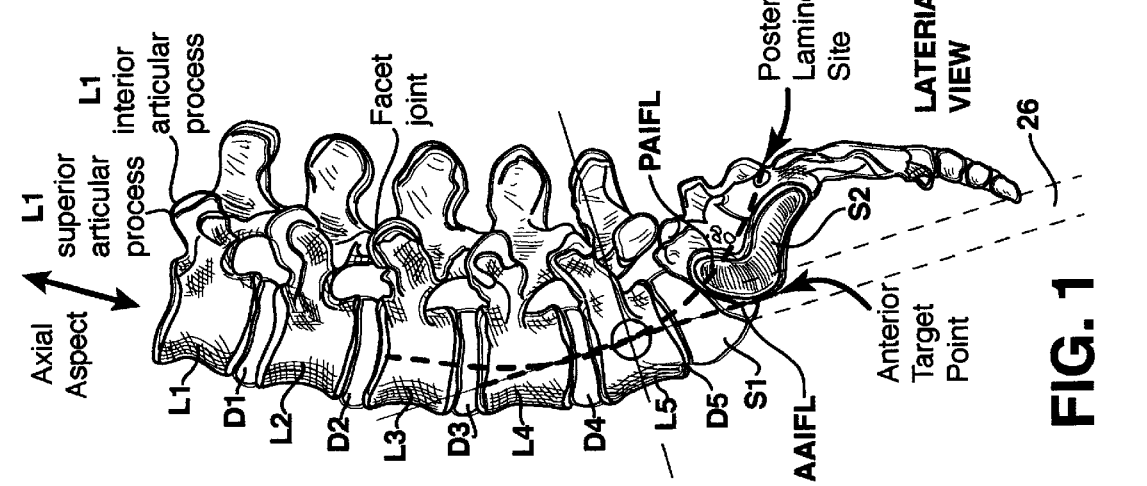

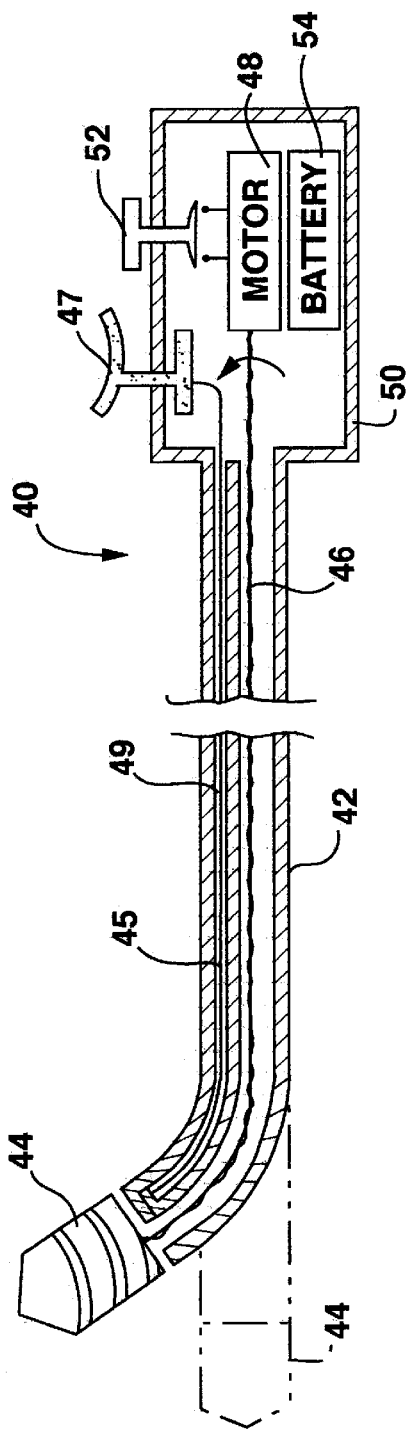
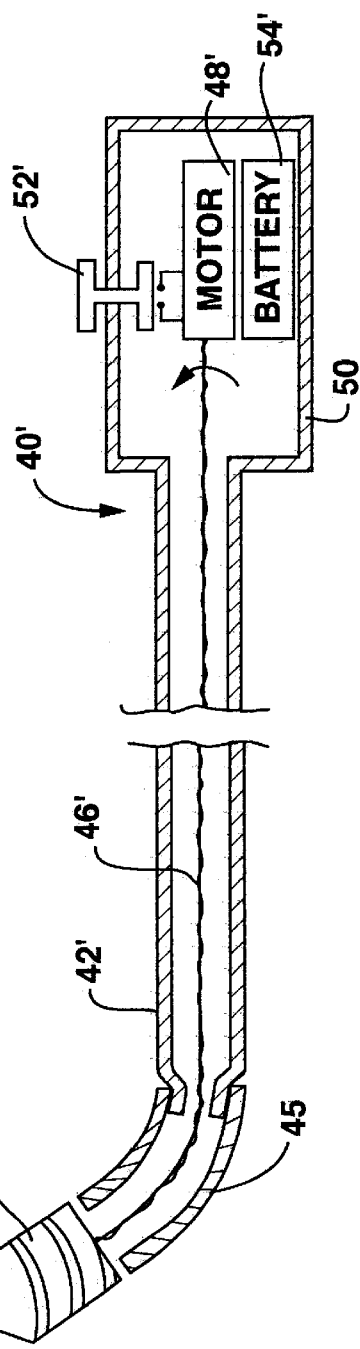
FIG. 9
FIG. 10

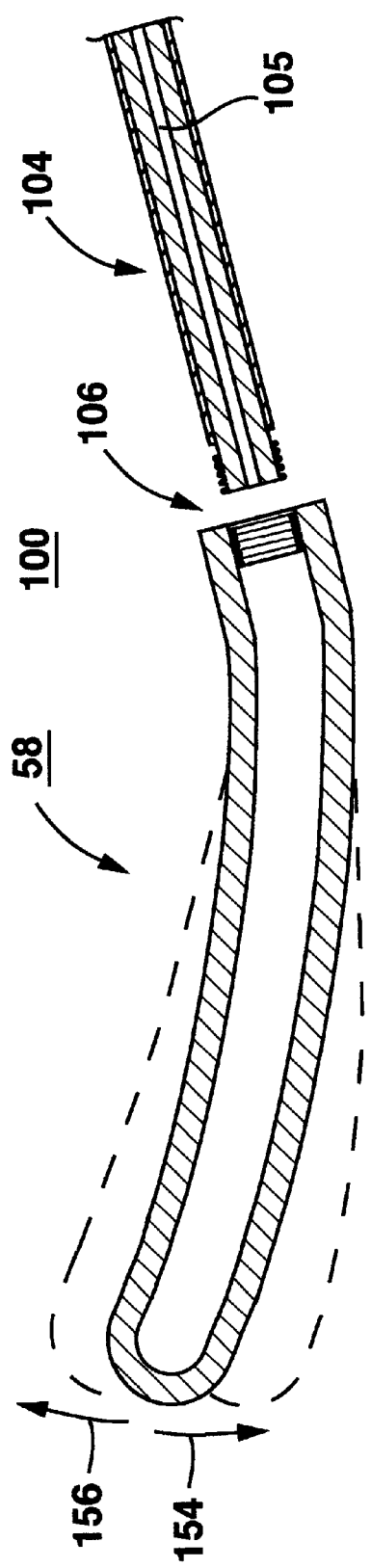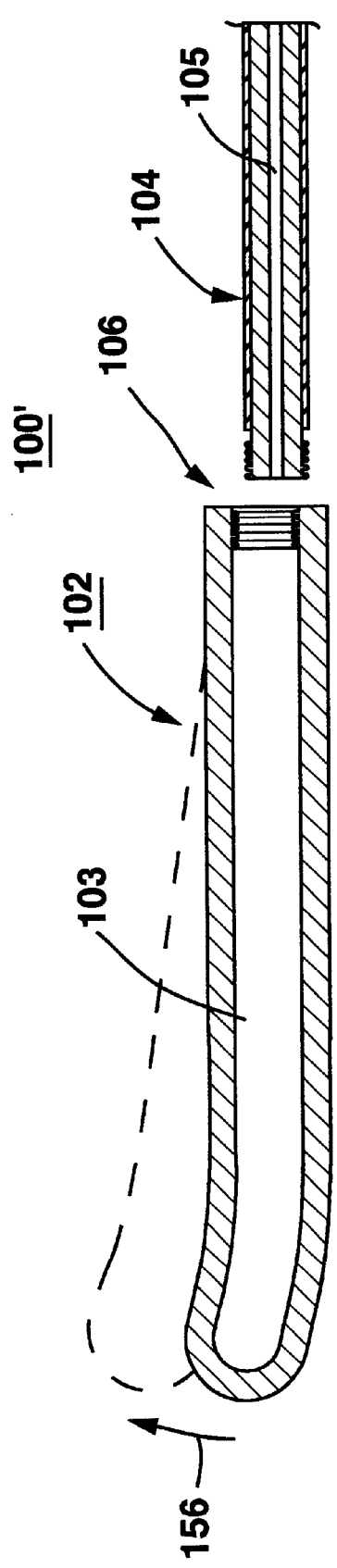

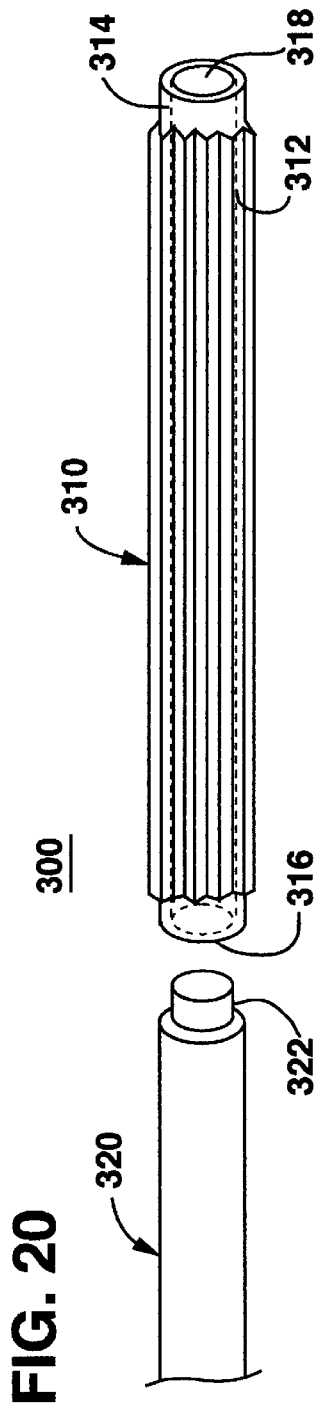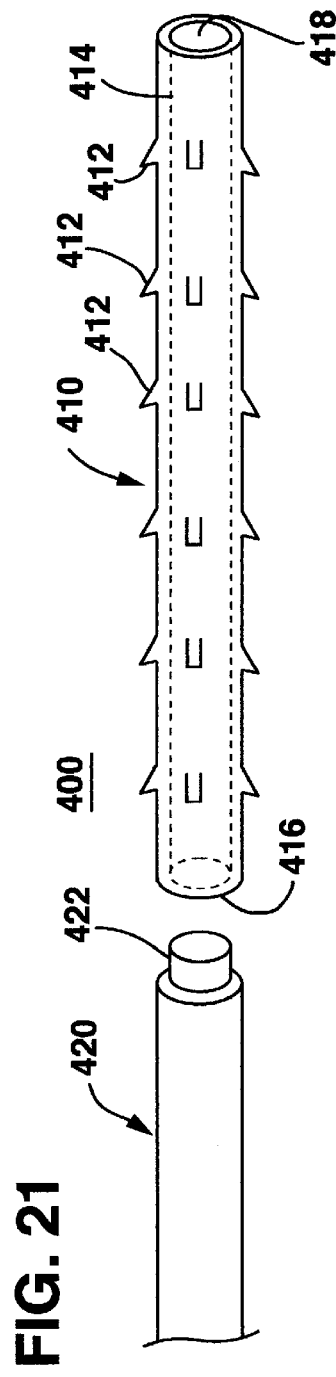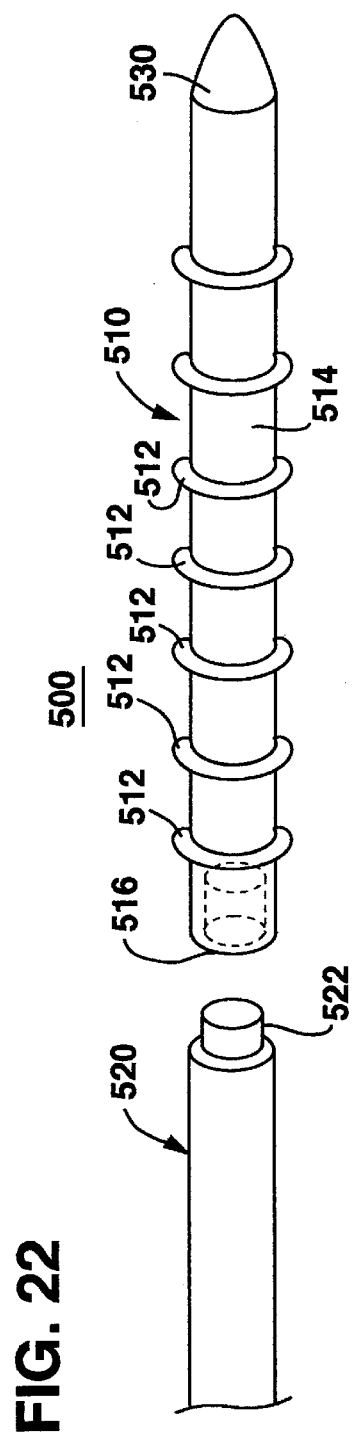

AXIAL SPINAL IMPLANT AND METHOD AND APPARATUS FOR IMPLANTING AN AXIAL SPINAL IMPLANT WITHIN THE VERTEBRAE OF THE SPINE

This application claims priority and benefits from Provisional Patent Application No. 60/182,748, filed Feb. 16, 2000 entitled METHOD AND APPARATUS FOR TRANS-SACRAL SPINAL FUSION.

FIELD OF THE INVENTION

The present invention relates generally to spinal implants for fusing and/or stabilizing spinal vertebrae and methods and apparatus for implanting one or more of such spinal implants axially within one or more axial bore within vertebral bodies in alignment with a visualized, trans-sacral axial instrumentation/fusion (TASIF) line in a minimally invasive, low trauma, manner.

BACKGROUND OF THE INVENTION

It has been estimated that 70% of adults have had a significant episode of back pain or chronic back pain emanating from a region of the spinal column or backbone. Many people suffering chronic back pain or an injury requiring immediate intervention resort to surgical intervention to alleviate their pain.

The spinal column or back bone encloses the spinal cord and consists of 33 vertebrae superimposed upon one another in a series which provides a flexible supporting column for the trunk and head. The vertebrae cephalad (i.e., toward the head or superior) to the sacral vertebrae are separated by fibrocartilaginous intervertebral discs and are united by articular capsules and by ligaments. The uppermost seven vertebrae are referred to as the cervical vertebrae, and the next lower twelve vertebrae are referred to as the thoracic, or dorsal, vertebrae. The next lower succeeding five vertebrae below the thoracic vertebrae are referred to as the lumbar vertebrae and are designated L1–L5 in descending order. The next lower succeeding five vertebrae below the lumbar vertebrae are referred to as the sacral vertebrae and are numbered S1–S5 in descending order. The final four vertebrae below the sacral vertebrae are referred to as the coccygeal vertebrae. In adults, the five sacral vertebrae fuse to form a single bone referred to as the sacrum, and the four rudimentary coccyx vertebrae fuse to form another bone called the coccyx or commonly the "tail bone". The number of vertebrae is sometimes increased by an additional vertebra in one region, and sometimes one may be absent in another region.

Typical lumbar, thoracic and cervical vertebrae consist of a ventral or vertebral body and a dorsal or neural arch. In the thoracic region, the ventral body bears two costal pits for reception of the head of a rib on each side. The arch which encloses the vertebral foramen is formed of two pedicles and two lamina. A pedicle is the bony process which projects backward or anteriorly from the body of a vertebra connecting with the lamina on each side. The pedicle forms the root of the vertebral arch. The vertebral arch bears seven processes: a dorsal spinous process, two lateral transverse processes, and four articular processes (two superior and two inferior). A deep concavity, inferior vertebral notch, on the inferior border of the arch provides a passageway or spinal canal for the delicate spinal cord and nerves. The successive vertebral foramina surround the spinal cord. Articulating processes of the vertebrae extend posteriorly of the spinal canal.

The bodies of successive lumbar, thoracic and cervical vertebrae articulate with one another and are separated by intervertebral discs formed of fibrous cartilage enclosing a central mass, the nucleus pulposus that provides for cushioning and dampening of compressive forces to the spinal column. The intervertebral discs are anterior to the vertebral canal. The inferior articular processes articulate with the superior articular processes of the next succeeding vertebra in the caudal (i.e., toward the feet or inferior) direction. Several ligaments (supraspinous, interspinous, anterior and posterior longitudinal, and the ligamenta flava) hold the vertebrae in position yet permit a limited degree of movement.

The relatively large vertebral bodies located in the anterior portion of the spine and the intervertebral discs provide the majority of the weight bearing support of the vertebral column. Each vertebral body has relatively strong bone comprising the outside surface of the body and weak bone comprising the center of the vertebral body.

Various types of spinal column disorders are known and include scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in the lumbar or cervical spine) and other disorders, such as ruptured or slipped discs, degenerative disc disease, fractured vertebra, and the like. Patients who suffer from such conditions usually experience extreme and debilitating pain and often neurologic deficit in nerve function.

Approximately 95% of spinal surgery involves the lower lumbar vertebrae designated as the fourth lumbar vertebra ("L4"), the fifth lumbar vertebra ("L5"), and the first sacral vertebra ("S1"). Persistent low back pain is attributed primarily to degeneration of the disc connecting L5 and S1. There are two possible mechanisms whereby intervertebral disc lesions can instigate and propagate low back pain. The first theory proposes that the intervertebral disc itself produces pain through trauma or degeneration and becomes the primary source of low back pain. Proponents of this theory advocate removal of the painful disc to relieve the low back pain.

Two extensive procedures are available to remove the disc and fuse the adjacent vertebrae together. One method is to replace the disc with bone plugs by going through the spinal canal on either side of the central nerve bundle. This method requires extensive stripping of the paraspinal musculature. More importantly, there are extensive surgical manipulations within the spinal canal itself. Although the initial proponents of this approach report 90% excellent to good results, subsequent studies have been unable to obtain acceptable outcomes and recommend adding internal fixation to improve fusion rates.

The second procedure is the anterior lumbar fusion which avoids the morbidity of posterior muscle stripping by approaching the spine through the abdomen. Surgeons experienced with this technique also report good to excellent patient results in 90% of cases performed. However, when generally used by practicing surgeons, the procedure was found to have a high failure rate of fusion. Attempts to increase the fusion rate by performing a posterior stabilization procedure have been successful, but the second incision increases the morbidity and decreases the advantages of the technique. Thus, the present surgical techniques available to remove and fuse painful lumbar discs are extensive operative procedures with potentially significant complications.

The other proposed mechanism for the intervertebral disc to cause low back pain concerns its affect on associated supportive tissues. The theory states that disc narrowing leads to stress on all of the intervertebral structures. These include the vertebral bodies, ligamentous supports, and facet joints. Surgeries designed to fuse and stabilize the intervertebral segment can be performed through the posterior approach. This is the original surgical procedure which was used to treat low back pain, and it also entails extensive muscular stripping and bone preparation.

There is no single procedure which is universally accepted to surgically manage low back pain patients. Although damaged discs and vertebral bodies can be identified with sophisticated diagnostic imaging, the surgical procedures are so extensive that clinical outcomes are not consistently satisfactory. Furthermore, patients undergoing presently available fusion surgery experience uncomfortable, prolonged convalescence.

A number of devices and techniques involving implantation of spinal implants to reinforce or replace removed discs and/or anterior portions of vertebral bodies and which mechanically immobilize areas of the spine assisting in the eventual fusion of the treated adjacent vertebrae have also been employed or proposed over the years In order to overcome the disadvantages of purely surgical techniques. Such techniques have been used effectively to treat the above described conditions and to relieve pain suffered by the patient. However, there are still disadvantages to the present fixation implants and surgical implantation techniques. The historical development of such implants is set forth in U.S. Pat. Nos. 5,505,732, 5,514,180, and 5,888,223, for example, all incorporated herein by reference.

One technique for spinal fixation includes the immobilization of the spine by the use of spine rods of many different configurations that run generally parallel to the spine. Typically, the posterior surface of the spine is isolated and bone screws are first fastened to the pedicles of the appropriate vertebrae or to the sacrum and act as anchor points for the spine rods. The bone screws are generally placed two per vertebra, one at each pedicle on either side of the spinous process. Clamp assemblies join the spine rods to the screws. The spine rods are generally bent to achieve the desired curvature of the spinal column. Wires may also be employed to stabilize rods to vertebrae. These techniques are described further in U.S. Pat. No. 5,415,661, for example, incorporated herein by reference.

These types of rod systems can be effective, but require a posterior approach and implanting screws into or clamps to each vertebra over the area to be treated. To stabilize the implanted system sufficiently, one vertebra above and one vertebra below the area to be treated are often used for implanting pedicle screws. Since the pedicles of vertebrae above the second lumbar vertebra (L2) are very small, only small bone screws can be used which sometimes do not give the needed support to stabilize the spine. These rods and screws and clamps or wires are surgically fixed to the spine from a posterior approach, and the procedure is difficult. A large bending moment is applied to such rod assemblies, and because the rods are located outside the spinal column, they depend on the holding power of the associated components which can pull out of or away from the vertebral bone.

In a variation of this technique disclosed in U.S. Pat. Nos. 4,553,273 and 4,636,217 (both described in U.S. Pat. No. 5,735,899 incorporated herein by reference, two of three vertebrae are joined by surgically obtaining access to the interior of the upper and lower vertebral bodies through excision of the middle vertebral body. In the '899 patent, these approaches are referred to as "intraosseous" approaches, although they are more properly referred to as "interosseous" approaches by virtue of the removal of the middle vertebral body. The removal is necessary to enable a lateral insertion of the implant into the space it occupied so that the opposite ends of the implant can be driven upward and downward into the upper and lower vertebral bodies. These approaches are criticized as failing to provide adequate medial-lateral and rotational support in the '899 patent. In the '889 patent, an anterior approach is made, slots are created in the upper and lower vertebrae, and rod ends are fitted into the slots and attached to the remaining vertebral bodies of the upper and lower vertebrae by laterally extending screws.

A wide variety of anterior, extraosseous fixation implants, primarily anterior plate systems, have also been proposed or surgically used. One type of anterior plate system involves a titanium plate with unicortical titanium bone screws that lock to the plate and are placed over the anterior surface of a vertebral body. Another type of anterior plate system involves the use of bicortical screws that do not lock to the plate. The bone screws have to be long enough to bite into both sides of the vertebral body to gain enough strength to obtain the needed stability. These devices are difficult to place due to the length of the screws, and damage occurs when the screws are placed improperly.

A number of disc shaped replacements or artificial disc implants and methods of insertion have been proposed as disclosed, for example, in U.S. Pat. Nos. 5,514,180 and 5,888,223, for example. A further type of disc reinforcement or augmentation implant that has been clinically employed for spinal fusion comprises a hollow cylindrical titanium cage that is externally threaded and is screwed laterally into place in a bore formed in the disc between two adjacent vertebrae. Bone grafts from cadavers or the pelvis or substances that promote bone growth are then packed into the hollow center of the cage to encourage bone growth (or ingrowth) through the cage pores to achieve fusion of the two adjacent vertebrae. Two such cage implants and the surgical tools employed to place them are disclosed in U.S. Pat. Nos. 5,505,732 and 5,700,291, for example. The cage implants and the associated surgical tools and approaches require precise drilling of a relatively large hole for each such cage laterally between two adjacent vertebral bodies and then threading a cage into each prepared hole. The large hole or holes can compromise the integrity of the vertebral bodies, and if drilled too posteriorly, can injure the spinal cord. The end plates of the vertebral bodies, which comprise very hard bone and help to give the vertebral bodies needed strength, are usually destroyed during the drilling. The cylindrical cage or cages are now harder than the remaining bone of the vertebral bodies, and the vertebral bodies tend to collapse or "telescope," together. The telescoping causes the length of the vertebral column to shorten and can cause damage to the spinal cord and nerves that pass between the two adjacent vertebrae.

Methods and apparatus for accessing the discs and vertebrae by lateral surgical approaches are described in U.S. Pat. No. 5,976,146. The intervening muscle groups or other tissues are spread apart by a cavity forming and securing tool set disclosed in the '146 patent to enable endoscope aided, lateral access to damaged vertebrae and discs and to perform corrective surgical procedures.

R. Johnsson et al. report the results of the use of biodegradable rods to augment posterolateral fusion of L5–S1 or L4–S1 in "Posterolateral lumbar fusion using facet joint fixation with biodegradeable rods: a pilot study" *Eur Spine J* 6:14–48'(1997). In this surgical technique, the posterolateral surfaces of the lumbrosacral spine were exposed, and two canals were bored through facets of the vertebrae to be fused. A rod formed of self-reinforced polyglycolic acid composite material was inserted through each canal, and fixed by absorption of body fluids and expansion therein. While successful fusion of L5–S1 was reported in a number of cases, fusion of L4–S1 was unsuccessful or inadequate, and lateral surgical exposure and stripping of the vertebrae facets was still necessary.

A compilation of the above described surgical techniques and spinal implants and others that have been used clinically is set forth in certain chapters of the book entitled *Lumbosacral and Spinopelvic Fixation*, edited by Joseph Y. Margolies et al. (Lippincott-Raven Publishers, Philadelphia., 1996). Attention is directed particularly to Chapters 1, 2, 16, 18, 38, 42 and 44. In Lumbopelyic Fusion" (Chapter 38, by Prof. Rene P. Louis, Md.) techniques for repairing a spondylolisthesis, in this case, a severe displacement of L5 with respect to S1 and the intervening disc, are described and depicted. An anterior lateral exposure of L5 and S1 is made, a discectomy is performed, and the orientation of L5 to S1 is mechanically corrected using a reduction tool, if the displacement is severe. A fibula graft or metal Judet screw is inserted as a dowel through a bore formed extending caudally through L5 and into S1. When the screw is used, bone growth material, e.g., bone harvested from the patient, is inserted into the bore alongside the screw, and the disc space is filled with bone sutured to the screw to keep it in place between the vertebral surfaces to act as a spacer implant occupying the extracted disc between L5 and S1. External bridge plates or rods are also optionally installed.

The posterolateral or anterior lateral approach is necessitated to correct the severe spondylolisthesis displacement using the reduction tool and results in tissue injury. Because of this approach and need, the caudal bore and inserted the Judet screw can only traverse L5 and S1.

A similar anterior approach for treating spondylolisthesis is disclosed in U.S. Pat. No. 6,056,749. In this approach, a bore hole is formed in a cephalad vertebral body and extends through the intervening disc into a caudal vertebral body, the disc is removed, a disk cage is inserted laterally into the disc space, and an elongated, hollow threaded shaft is inserted into the bore and through a hole in the disc cage. The disk cage takes the place of the harvested bone disc inserts and its interlocking intersection with the shaft takes the place of the sutures employed to tie the harvested bone disc inserts to the screw in the technique described in the above-referenced Chapter 38 publication.

The above-described spinal implant approaches involye highly invasive surgery that laterally exposes the anterior or posterior portions of the vertebrae to be supported or fused. Extensive muscular stripping and bone preparation can be necessary. As a result, the spinal column can be further weakened and/or result in surgery induced pain syndromes. Thus, presently used or proposed surgical fixation and fusion techniques involving the lower lumbar vertebrae suffer from numerous disadvantages. It is preferable to avoid the lateral exposure to correct less severe spondylolisthesis and other spinal injuries or defects affecting the lumbar and sacral vertebrae and discs.

A less intrusive posterior approach for treating spondylolisthesis is disclosed in U.S. Pat. No. 6,086,589, wherein a straight bore is formed through the sacrum from the exposed posterior sacral surface and in a slightly cephalad direction into the L5 vertebral body, preferably after realigning the vertebrae. A straight, hollow, threaded shaft with side wall holes restricted to the end portions thereof and bone growth material are inserted into the bore. A discectomy of the disc between L5 and S1 is preferably performed and bone ingrowth material is also preferably inserted into the space between the cephalad and caudal vertebral bodies. Only a limited access to and alignment of S1 and L5 can be achieved by this approach because the distal ends of the straight bore and shaft approach and threaten to perforate the anterior surface of the L5 vertebral body.

A wide variety of orthopedic implants have also been proposed or clinically employed to stabilize broken bones or secure artificial hip, knee and finger joints. Frequently, rods or joint supports are placed longitudinally within longitudinal bores made in elongated bones, e.g., the femur. A surgical method is disclosed in U.S. Pat. No. 5,514,137 for stabilizing a broken femur or other long bones using an elongated rod and resorbable cement. To accomplish a placement of a rod into any single bone, an end of a bone is exposed and a channel is drilled from the exposed end to the other end. Thereafter, a hollow rod is inserted, and resorbable cement is injected through the hollow rod, so as to provide fixation between the distal end of the rod and the cancellous tissue that surrounds the rod. A cement introducer device can also be used for the injection of cement. A brief reference is made in the '137 patent to the possibility of placing rods in or adjacent to the spine in the same manner, but no particular approach or devices are described.

The present invention has at least one objective of providing practical and advantageous spinal implants and implantation systems, methods and tools for accessing the spinal vertebrae to insert spinal implants in various manners that overcome the above described disadvantages of posterior and anterior lateral approaches thereto and minimize surgical trauma to the patient.

SUMMARY OF THE INVENTION

The preferred embodiments of the invention involye methods and apparatus for inserting longitudinal TASIF spinal prostheses or implants axially through a series of vertebral bodies and intervening discs, unless they are removed or missing, and various forms of the spinal implants, referred to at times as rods or prostheses herein.

A number of differing types of TASIF spinal implants can be inserted into TASIF axial bore or bores or pilot holes that are formed in a variety of manners preferably through a posterior or anterior trans-sacral approach. The spinal implants therapeutically align or strengthen or fuse or maintain separation (traction) between the adjacent vertebrae particularly in the lumbar region of the spinal column.

A wide variety of pre-formed spinal implants fabricated from bio-compatible implant materials can be inserted into the TASIF axial bore or bores or pilot holes. Preferably, attachment mechanisms are provided that attach or affix or force the pre-formed spinal implants or rods to or against the vertebral bone along the full length of the TASIF axial bore or bores or pilot holes or at the cephalad end and/or caudal end of the TASIF axial bore or bores or pilot holes. The attachment mechanism can be an external surface configuration of the spinal implant body that is adapted to engage the vertebral body along at least a portion of the length of the spinal implant body. The engagement of the vertebral body is either an active engagement upon implantation of the spinal implant into the TASIF axial bore or a passive engagement of the external surface configuration with the vertebral bone caused by bone growth about the external surface configuration.

A plurality of such spinal implants can be inserted axially in the same TASIF axial bore or pilot hole or separately in a plurality of TASIF axial bores or pilot holes that extend axially and in a side-by-side relation through the vertebrae and discs, if present, between the vertebrae.

Discectomies and/or vertebroblasty can be performed through the TASIF axial bore or bores or pilot holes prior to insertion of the spinal implants. Vertebroblasty is a procedure for augmentation of collapsed vertebral bodies by pumped-in materials, e.g., bone cement or bone growth materials. Materials or devices can also be delivered into the disc space to separate the adjoining vertebrae and/or into damaged vertebral bodies or to strengthen them.

The axially extending TASIF spinal implants reinforce the relatively strong anterior vertebral bodies and should prevent potentially damaging telescoping of adjacent vertebrae. The TASIF spinal implants can be implanted in accordance with the present invention in a less traumatic manner than conventional lateral exposure and placement of conventional vertebral prostheses, and the need to implant screws or extend wires laterally through the vertebral bodies and a rod or rods is eliminated. Unlike conventional spinal rods, the TASIF spinal implants inherently possess a low profile and would usually not be felt by the patient after healing.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIGS. 1–3 are lateral, posterior and anterior views of the lumbar and sacral portion of the spinal column depicting the visualized PAIFL and AAIFL extending cephalad and axially from the posterior laminectomy site and the anterior target point, respectively;

FIG. 4 is a sagittal caudal view of lumbar vertebrae depicting a TASIF spinal implant or rod within a TASIF axial bore formed following the visualized PAIFL or AAIFL of FIGS. 1–3;

FIG. 5 is a sagittal caudal view of lumbar vertebrae depicting a plurality, e.g., 2, TASIF spinal implants or rods within a like plurality of TASIF axial bores formed in parallel with the visualized PAIFL or AAIFL of FIGS. 1–3;

FIG. 7 illustrates one exemplary method of step S100 of FIG. 6 for providing a posterior percutaneous pathway to the posterior target point of the posterior sacrum that the curved PAIFL commences from;

FIGS. 9 and 10 are views of alternate embodiments of a motor driven, canted tip, drill for drilling the posterior or anterior TASIF axial bores following the visualized PAIFL or AAIFL FIGS. 1–5;

FIGS. 12 and 13 illustrate embodiments of posterior and anterior TASIF spinal implants formed of shape memory or superelastic alloy adapted to assume differing curvatures at implantation and body temperatures and insertion tools for inserting the same into posterior and anterior TASIF axial bores;

FIG. 20 illustrates a further embodiment of a straight anterior or curved posterior or anterior TASIF spinal implant having a plurality of elongated flutes extending along its outer surface through the full length or one or more portion of the length of the spinal implant body and an insertion tool for inserting the same into a curved anterior or posterior TASIF axial bore;

FIG. 21 illustrates a further embodiment of a straight anterior or curved posterior or anterior TASIF spinal implant having a plurality of outwardly extending barbs arranged along its outer surface through the full length or one or more portion of the length of the spinal implant body and an insertion tool for inserting the same into a curved anterior or posterior TASIF axial bore;

FIG. 22 illustrates a further embodiment of a straight anterior or curved posterior or anterior TASIF spinal implant having a plurality of outwardly extending flanges arranged along its outer surface through the full length or one or more portion of the length of the spinal implant body and an insertion tool for inserting the same into a curved anterior or posterior TASIF axial bore;

DETAILED DESCRIPTION OF THE PREFERRED EMBODIMENTS OF THE INVENTION

Figure 6:
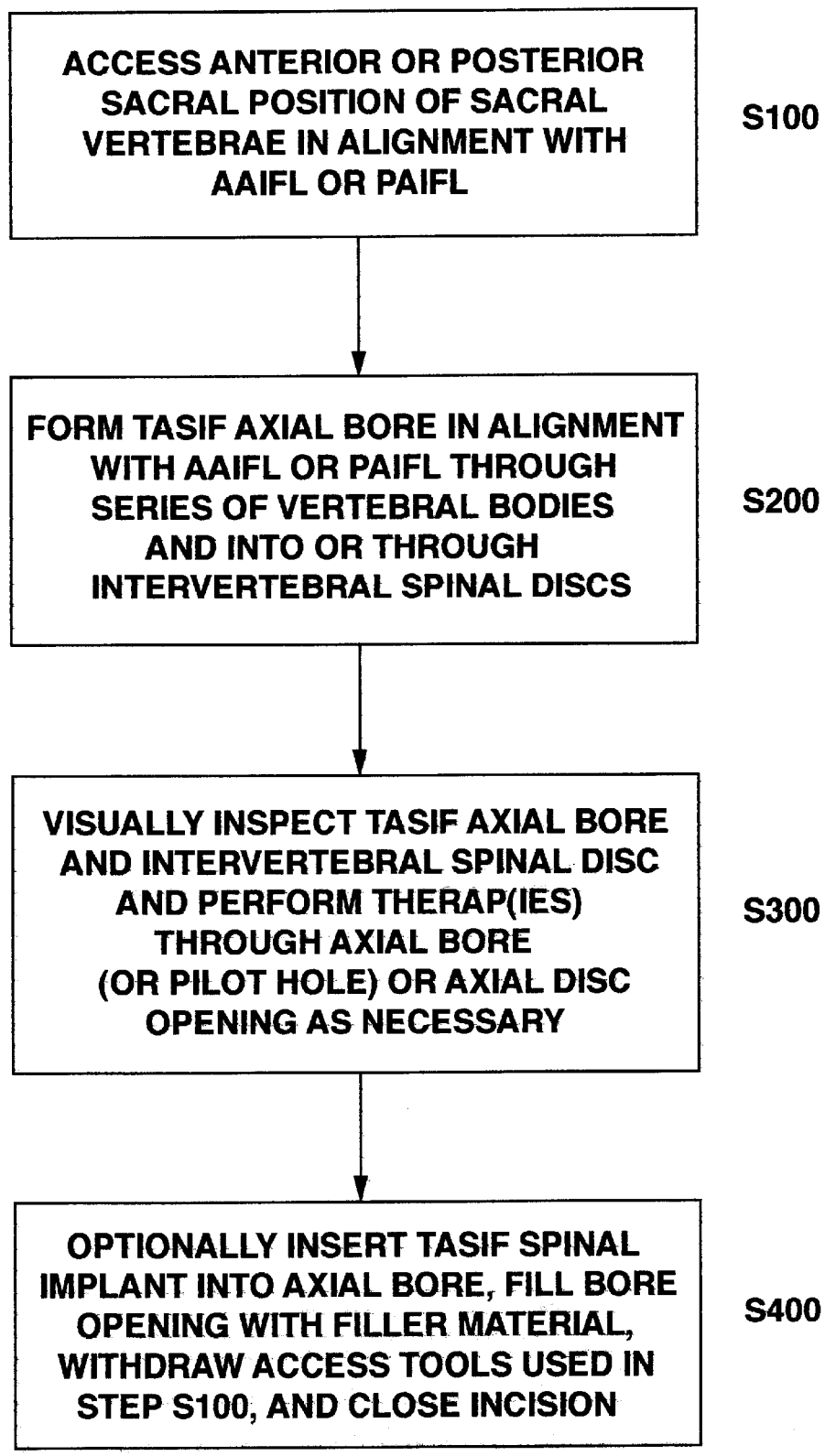
FIG. 6 is a simplified flow chart showing the principal surgical preparation steps of percutaneously accessing a posterior or anterior target point of the sacrum and forming a percutaneous tract following the visualized PAIFL or AAIFL of FIGS. 1–3, as well as subsequent steps of forming the TASIF bore(s) for treatment of accessed vertebral bodies and intervening discs and of implanting spinal implants therein.

The methods and surgical instrumentation and spinal implants disclosed in the above-referenced provisional application No. 60/182,748 and in co pending, commonly assigned application Ser. No. 09/640,222 filed Aug. 16, 2000, for METHOD AND APPARATUS FOR PROVIDING POSTERIOR OR ANTERIOR TRANS-SACRAL ACCESS TO SPINAL VERTEBRAE can be employed in the practice of the present invention. The '222 application discloses a number of related TASIF methods and surgical tool sets for providing posterior and anterior trans-sacral access to a series of adjacent vertebrae located within a human lumbar and sacral spine having an anterior aspect, a posterior aspect and an axial aspect, the vertebrae separated by intact or damaged spinal discs. Certain of the tools are selectively employed to form a percutaneous (i.e., through the skin) pathway from an anterior or posterior skin incision to a respective anterior or posterior position, e.g., a target point of a sacral surface or the cephalad end of a pilot hole bored through the sacrum and one or more lumbar vertebrae. The percutaneous pathway is generally axially aligned with an anterior axial instrumentation/fusion line (AAIFL) or a posterior axial instrumentation/fusion line (PAIFL) extending from the respective anterior or posterior target point through at least one sacral vertebral body and one or more lumbar vertebral body in the cephalad direction and visualized by radiographic or fluoroscopic equipment. The AAIFL and PAIFL follow the curvature of the vertebral bodies, although the AAIFL can be straight or relatively straight, depending on the number of vertebrae that the AAIFL is extended through.

The preferred embodiments of the present invention involve methods and apparatus including surgical tool sets for forming anterior and posterior TASIF axial bores in alignment with the visualized AAIFL and PAIFL and the insertion of spinal implants therein. In certain embodiments, pilot holes may be bored in the cephalad direction through one or more sacral and lumbar vertebral bodies in alignment with the visualized AAIFL and PAIFL and used as part of the anterior and posterior percutaneous tracts used to form the TASIF axial bores which are also referred to as TASF bores in the above-referenced parent provisional application No. 60/182,748.

As noted above and shown in the above-referenced provisional application No. 60/182,748, the pilot holes of the anterior and posterior percutaneous tracts can be used to introduce instruments to inspect and/or perform therapies upon the vertebral bodies or intervening discs. The posterior or anterior pilot hole may optionally be used as the posterior or anterior TASIF axial bore, respectively, axially aligned with the PAIFL or AAIFL, respectively, to receive spinal implants of various types.

The following description of FIGS. 1–6 is taken from the above-referenced parent provisional application No. 60/182, 748. The acronyms TASF, AAFL, and PAFL are changed to TASIF, AAIFL and PAIFL in this application to explicitly acknowledge that instruments can be introduced for inspection or treatments in addition to the fusion and fixation provided by spinal implants that may be inserted into the axial bores or pilot holes.

FIGS. 1–3 schematically illustrate the anterior and posterior TASIF surgical approaches in relation to the lumbar region of the spinal column, and FIGS. 4–5 illustrate the location of the TASIF implant or pair of TASIF implants within a corresponding posterior or anterior TASIF axial bore 22 or 152 or pair of TASIF axial bores $22_1$, $22_2$ or $152_1$, $152_2$. Preferred TASIF surgical approaches for providing anterior and posterior trans-sacral access depicted in FIGS. 1–3 and preparing the TASIF axial bores 22 or 152 or $22_1$, $22_2$, or $152_1$, $152_2$ shown in FIGS. 4 and 5 are illustrated in further drawings. Preferred trans-sacral surgical access and TASIF pilot hole preparation tools are depicted in further drawings. Two TASIF axial bores and spinal implants or rods are shown in FIG. 5 to illustrate that a plurality, that is two or more, of the same may be formed and/or employed in side by side relation parallel with the AAIFL or PAIFL.

The lower regions of the spinal column comprising the coccyx, fused sacral vertebrae S1–S5 forming the sacrum, and the lumbar vertebrae L1–L5 described above are depicted in a lateral view in FIG. 1. The series of adjacent vertebrae located within the human lumbar and sacral spine have an anterior aspect, a posterior aspect and an axial aspect, and the lumbar vertebrae are separated by intact or damaged spinal discs labeled D–D5 in FIG. 1. FIGS. 2 and 3 depict the posterior and anterior view of the sacrum and coccyx.

In accordance with the present invention, the method and apparatus for inserting one or more spinal implant or rod axially through at least L4 and L5 and optionally performing a discectomy of D5 and/or D4 involves accessing an anterior sacral position, e.g. an anterior target point at the junction of S1 and S2 depicted in FIGS. 1 and 3, or a posterior sacral position, e.g. a posterior laminectomy site of S2 depicted in FIGS. 1 and 2. One (or more) visualized, imaginary, axial instrumentation/fusion line extends cephalad and axially in the axial aspect through the series of adjacent vertebral bodies to be fused, L4 and L5 in this illustrated example. The visualized AAIFL through L4, D4, L5 and D5 extends relatively straight from the anterior target point along S1 depicted in FIGS. 1 and 3, but may be curved as to follow the curvature of the spinal column in the cephalad direction. The visualized PAIFL extends in the cephalad direction with more pronounced curvature from the posterior laminectomy site of S2 depicted in FIGS. 1 and 2.

It should be noted that the formation of the anterior tract 26 through presacral space under visualization described above is clinically feasible as evidenced by clinical techniques described by J. J. Trambert, MD, in "Percutaneous Interventions in the Presacral Space: CT-guided Precoccygeal Approach—Early Experience (*Radiology* 1999; 213:901–904).

FIG. 6 depicts, in general terms, the surgical steps of accessing the anterior or posterior sacral positions illustrated in FIGS. 1–3 (S100) forming posterior and anterior TASIF axial bores (S200), optionally inspecting the discs and vertebral bodies, performing disc removal, disc augmentation, and vertebral bone reinforcement (S300), and implanting posterior and anterior spinal implants and rods (S400) in a simplified manner. In step S100, access to the anterior or posterior sacral position, that is the anterior target point of FIG. 3 or the posterior laminectomy site of FIG. 2 is obtained, and the anterior or posterior sacral position is penetrated to provide a starting point for each axial bore that is to be created. Then, an axial bore is bored from each point of penetration extending along either the PAIFL or AAIFL cephalad and axially through the vertebral bodies of the series of adjacent vertebrae and any intervening spinal discs (S200). The axial bore may be visually inspected using an endoscope to determine if the procedures of step S300 should be performed. Discoscopy or discectomy or disc augmentation of an intervening disc or discs or vertebroblasty of a vertebral body may be performed through the axial bore (S300). Finally, an elongated TASIF spinal implant or rod is inserted into each axial bore to extend cephalad and axially through the vertebral bodies of the series of adjacent vertebrae and any intervening spinal discs (S400). Other types of spinal implants for delivering therapies or alleviating pain as described above may be implanted in substitution for step S400.

It should be noted that performing step S100 in the anterior and/or posterior TASIF procedures may involve drilling a pilot hole, smaller in diameter than the TASIF axial bore, that tracks the AAIFL and/or PAIFL in order to complete the formation of the anterior and/or posterior percutaneous tracts. Step S300 may optionally be completed through the AAIFL/PAIFL pilot hole following step S100, rather than following the enlargement of the pilot hole to form the TASIF axial bore in step S200.

Step S100 preferably involves creation an anterior or posterior percutaneous pathway that enables introduction of further tools and instruments for forming an anterior or posterior percutaneous tract extending from the skin incision to the respective anterior or posterior target point of the sacral surface or, in some embodiments, the cephalad end of a pilot hole over which or through which further instruments are introduced as described in the above-referenced 222 application. An "anterior, presacral, percutaneous tract" extends through the "presacral space" anterior to the sacrum. The posterior percutaneous tract or the anterior, presacral, percutaneous tract is preferably used to bore one or more respective posterior or anterior TASIF bore in the cephalad direction through one or more lumbar vertebral bodies and intervening discs, if present. A single anterior or posterior TASIF bore is preferably aligned axially with the respective visualized MIFL or PAIFL, and plural anterior or posterior TASIF bores are preferably aligned in parallel with the respective visualized AAIFL or PAIFL. Introduction of spinal implants and instruments for performing discectomies and/or disc and/or vertebral body augmentation is enabled by the provision of the percutaneous pathway and formation of the anterior or posterior TASIF bore(s).

Posterior TASIF Axial Bore Spinal Implant Implantation:

Step S100 of FIG. 6 performed in the posterior TASIF procedure involves forming a posterior percutaneous tract that preferably extends from a posterior skin incision into the posterior sacrum to a posterior target point exposed by a laminectomy. This posterior percutaneous tract has a tract axis aligned with the visualized PAIFL to provide working space, exposure of the sacrum, and alignment of the boring tool with the visualized PAIFL. The posterior percutaneous tract can take the form of a lumen of a tract sheath introduced through the percutaneous pathway or a guidewire whereby the guidewire provides a percutaneous tract for over the wire passage extending from the skin incision to the posterior target point and aligned with the visualized PAIFL. Either or both of the tract sheath or guidewire can comprise distal fixation mechanisms that enable fixation to the sacral vertebral surface at the posterior target point for through the sheath or over the wire introduction of boring tools or other instruments. Prior to boring the posterior TASIF bore(s), a pilot hole for each such posterior TASIF bore is optionally bored along or parallel with the visualized PAIFL, and the guidewire distal end is affixed to vertebral bone at the cephalad end of the pilot hole to provide the percutaneous tract for guiding a drill or other instrument to form the posterior TASIF bore or conduct discectomies or disc or vertebral bone augmentation.

Figure 7:
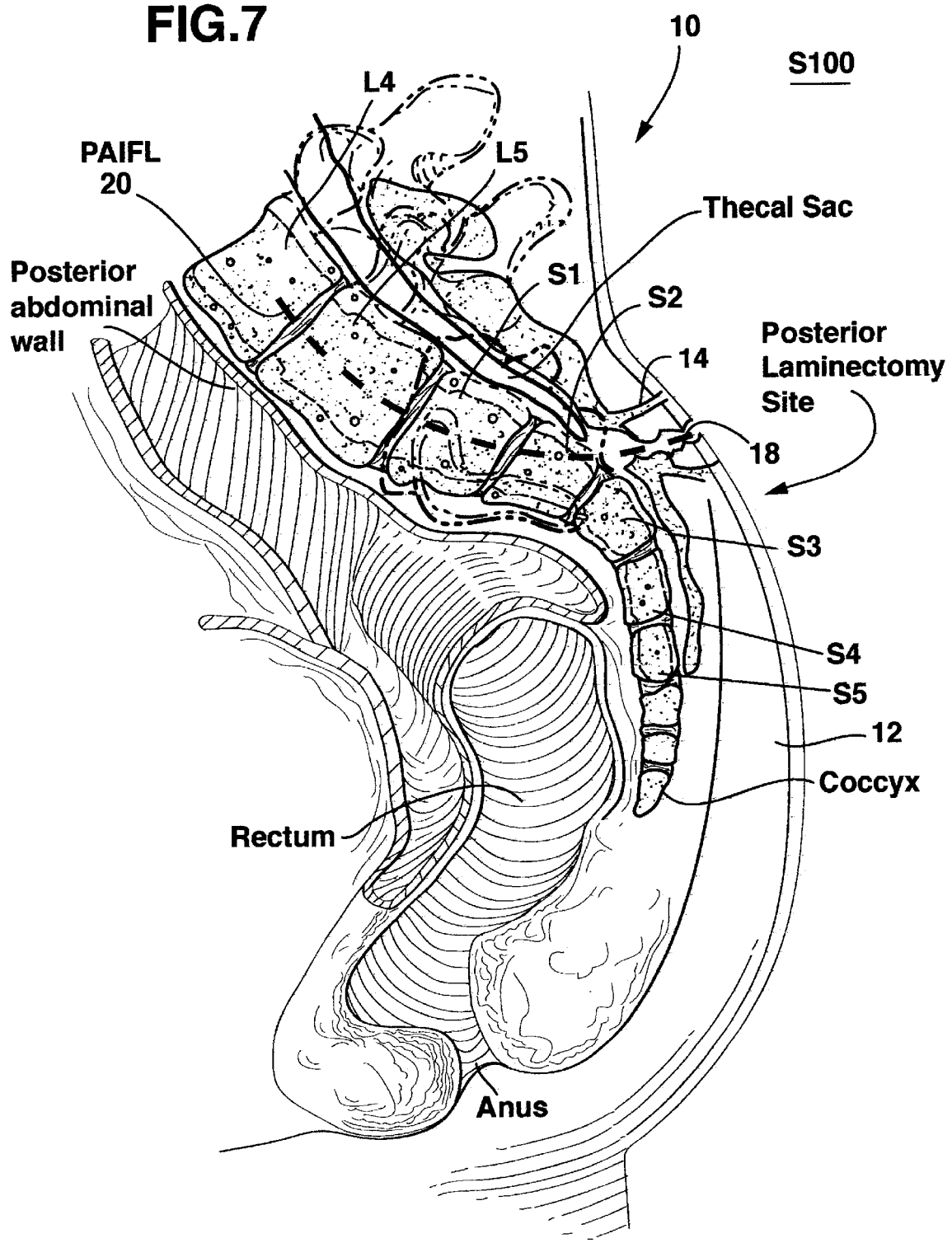

Turning to FIG. 7, it is expected that the patient 10, depicted in FIG. 7 in a partial side cross-section view, will lie prone on a surgical table having reverse lordosis support. An imaging system (not shown), which may be a CT scanner or bi-plane fluoroscopy machine, is employed first to show the spinal structure and adjacent tissues, vessels and nerves for visualizing the PAIFL through the visible landmarks of the sacrum and lumbar vertebrae. Then, the imaging system is employed during the surgical creation of the posterior TASIF axial bore to ensure that it remains within the vertebral bodies and intervening discs following the PAIFL and does not stray anteriorly, posteriorly or laterally therefrom.

The area of the patient's skin 12 surrounding the incision site is surgically prepped, and the anus is excluded from the surgical field using adhesive drapes. The actual dermal entry site may be determined by the prone, preoperative CT scan or MRI study that maps the PAIFL. In step S100, depicted in FIG. 7, an incision is made in the patient's skin 12 over the posterior sacral surface of S2 and a posterior tract 18 is formed through the subcutaneous tissue to expose the posteriorly extending, bony ridge of the posterior sacral surface. A small laminectomy 14 is performed through the posterior ridge of the sacrum inferior. The thecal sac and nerve roots that are exposed by the laminectomy are gently retracted, and the terminal portion of the spinal canal is exposed. A drill guide for receiving a drill bit and shaft for drilling or boring a TASIF axial bore from S2 along the visualized PAIFL 20 may optionally be attached to S2 and extended posteriorly through the exposed spinal canal and skin incision.

Figure 8:
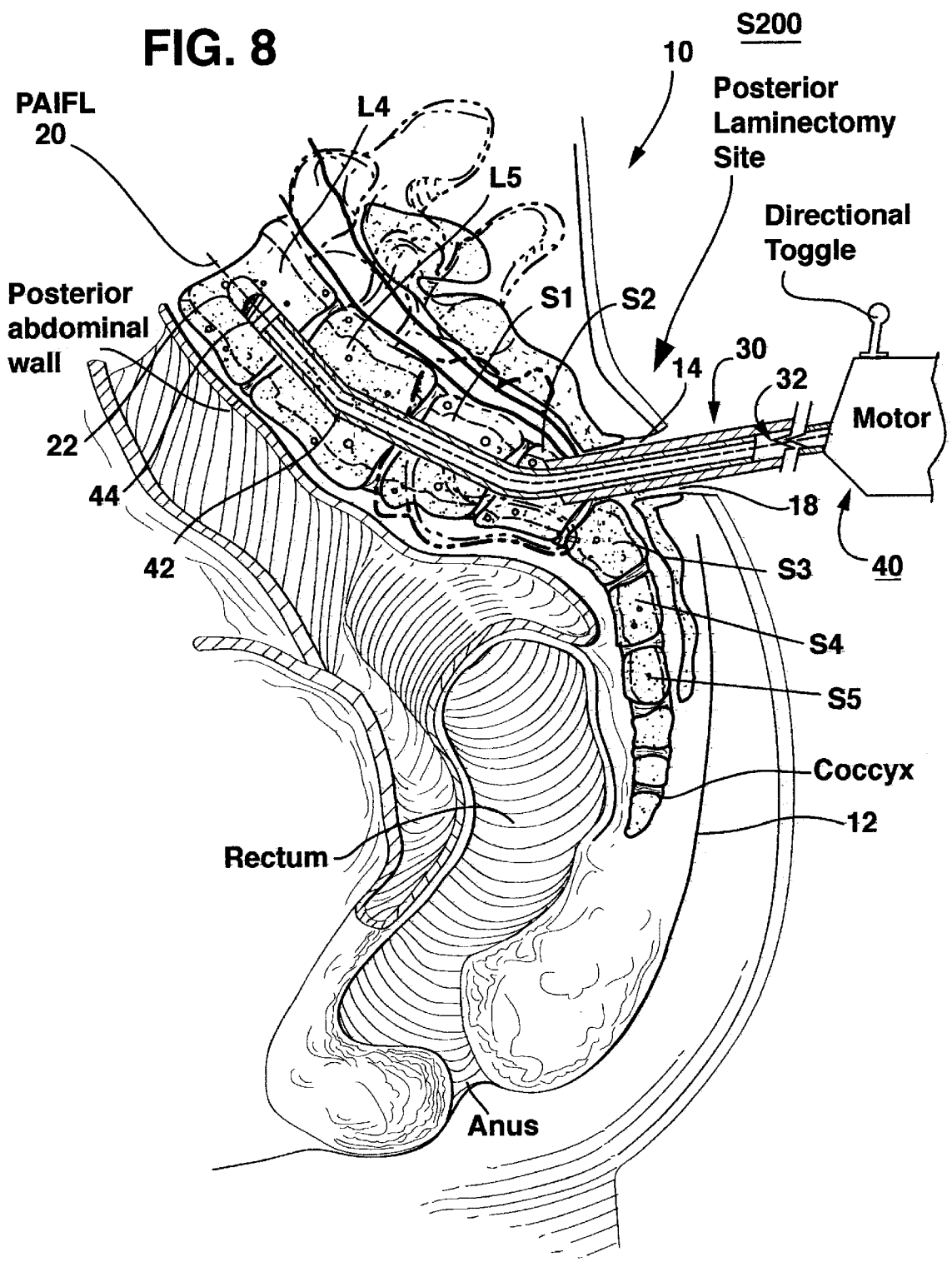
FIG. 8 illustrates one manner of forming the posterior TASIF axial bore through sacral and lumbar vertebrae and intervening discs axially aligned with the visualized PAIFL of FIGS. 1 and 2 in accordance with step S200 of FIG. 6.

FIG. 8 illustrates the formation of the posterior TASIF axial bore 22 in step S200 through the centers of two or more vertebral bodies L4, L5 and intervening discs anterior to and extending in parallel with the thecal sac (also shown in FIG. 4, for example). The posterior TASIF procedure illustrated in FIG. 8 requires a drill capable of drilling or another bore forming mechanism capable of forming the curved TASIF axial bore 22 and a curved TASIF spinal implant or rod 58 capable of being advanced through the curved posterior TASIF axial bore 22. The curved axial bore is made upwardly through S2, S1 and into at least L5 and optionally extended and curved to follow the curvature of the vertebrae L4, L3, et seq. in the cephalad direction. A curved TASIF implant or rod 58 can be inserted into the curved posterior TASIF axial bore 22 to bridge the vertebrae and the intervening discs, if present.

As shown in FIG. 8, the optional drill guide 30 having a drill guide sheath lumen 32 may be provided and extended through the posterior tract 18 and optionally attached at its distal end to a fixation hole 16 and is aligned axially with the PAIFL 20. A drill bit 44 at the distal end of a directional drill sheath 42 of a drill 40 or 40' (depicted in FIGS. 9 and 10) is carefully advanced using biplane fluoroscopic visualization through the drill guide sheath lumen 32 or directly through the posterior tract 18 if the drill guide sheath 30 is not used. The drill drive shaft 46, 46' within the drill sheath 42 is rotated by the drill motor to rotate the drill bit 44, 44' as it is advanced under fluoroscopic observation along the visualized PAIFL 20 and form the curved posterior TASIF axial bore 22.

Suitable exemplary directional drills 40 and 40' are schematically depicted in FIGS. 9 and 10. The drill 40 of FIG. 9 comprises a drill motor housing 50 coupled with drill sheath 42 enclosing the drill drive shaft 46. The drill motor housing 50 includes a motor 48 powered by a battery 54. The drill motor 48 is coupled to the battery 54 by manipulation of a power switch 52 to rotate the drive shaft 46 and drill bit 44 of drill 40. The drill sheath 42 and drive shaft 46 are flexible and can follow the curved posterior TASIF axial bore 22.

A pull wire 45 extends through a pull wire lumen 49 extending along one side of the sheath 42 between its distal end and a tip curvature control 47 on drill motor housing 50. The distal end portion of drill sheath 42 is flexible, and retraction of pull wire 45 by manipulation of tip curvature control 47 causes the distal end portion of drill sheath 42 to assume a curvature from the straight configuration as shown in phantom lines in FIG. 9. The surgeon can manipulate tip curvature control 47 to control the curvature of the distal end portion of drill sheath 42 and the TASIF axial bore 22. The flexible drill sheath 42 and drive shaft 46 can follow the curved posterior TASIF axial bore 22.

The drill 40' of FIG. 10 comprises a drill motor housing 50' coupled with drill sheath 42' enclosing the drill drive shaft 46'. The drill motor housing 50' includes a battery 54' and motor 48' that is turned on by manipulation of a power switch 52' to rotate the drive shaft 46' and drill bit 44' of drill 40'. In this embodiment, the distal end portion 56 of drill sheath 42' is pre-curved or canted at about 20°, for example, providing an eccentric drill bit 44'. The drill sheath 42' and drive shaft 46' are flexible and can follow the curved posterior TASIF axial bore 22 as it is formed.

The eccentric drill bit 44' has an inherent tendency to "veer" in the direction of rotation of the drill bit. Rotating the drill sheath 42' during advancement along the visualized axial fusion line 20 causes it to form the TASIF axial bore 22 that follows the curved PAIFL of FIGS. 1 and 8. The flexible drill sheath 42' and drive shaft 46' can follow the curved posterior TASIF axial bore 22.

The drilling of the posterior TASIF axial bore 22 may alternatively be undertaken in sequential steps of first drilling a small diameter pilot hole along the PAIFL 20 using the drill 40 or 40', inserting a guidewire through the pilot hole, and then enlarging the pilot hole to form the curved posterior TASIF axial bore. The posterior TASIF axial bore forming tool set may be similar to the anterior TASIF axial bore forming steps and tools described below. Using this technique to form the posterior TASIF axial bore, a small diameter drill bit and drill shaft (e.g. 3.0 mm diameter) is used to first drill a small diameter pilot hole following the imaginary, visualized PAIFL 20 through S1, L5 and L4. Then, the drill bit and shaft are removed, and a guidewire having a threaded distal screw-in tip is advanced through the pilot hole and screwed into to the caudal end of the pilot hole and into cephalad portion of the L4 body. An over-the-wire bore enlarging tool is fitted over the proximal end of the guidewire and manually or mechanically rotated and advanced along it in the manner described below with regard to the formation of the larger diameter, e.g. a 10.0 mm diameter, anterior TASIF axial bore 22. In this way, the pilot hole diameter is enlarged to form the anterior TASIF axial bore 22, and the enlarging tool is then removed.

Thus, the longitudinal, curved, posterior TASIF axial bore 22 that is formed in step S200 of FIG. 6 as described above in reference to FIGS. 7–10 starts in the sacrum at the posterior laminectomy site or target point and extends upwardly or cephalad through the vertebral body of S1 or S2 and through the cephalad vertebral bodies including L5 and L4 and the intervening discs denoted D4 and D5 in FIG. 1. Discs D4 and D5 are usually damaged or have degenerated between lumbar spine vertebrae and cause the pain experienced by patients requiring intervention and fusion of the vertebrae. An inspection of the vertebral bodies and discs along the sides of the TASIF axial bore 22 can be made using an elongated endoscope inserted through the TASIF axial bore 22 or the pilot hole if one is formed. A discectomy or disc augmentation and/or vertebroblasty may be performed pursuant to step S300 of FIG. 6 through the posterior TASIF axial bore 22 or pilot hole and laminectomy site to relieve the patient's symptoms and aid in the fusion achieved by the posterior spinal implant or rod 22. The discectomy and disc augmentation procedures that can be performed via either the anterior or posterior TASIF axial bore is described further below in reference to FIGS. 15 and 16.

The posterior TASIF spinal implant or rod that is implanted into the posterior TASIF axial bore 22 formed in step S200 and depicted in FIG. 8 is provided in a number of diameters, lengths and curvatures so that a suitable one may be selected for insertion into a particular TASIF axial bore 22 and may include a variety of fixation mechanisms. The curved TASIF spinal implant or rod 58 may be formed of autologous bone material or of a bio-compatible material customarily used for bone implants, e.g. titanium, a titanium alloy, e.g., Ti6AI-4Va alloy, or a shape memory or superelastic material, e.g. Nitinol Ni—Ti alloy.

Figure 11:
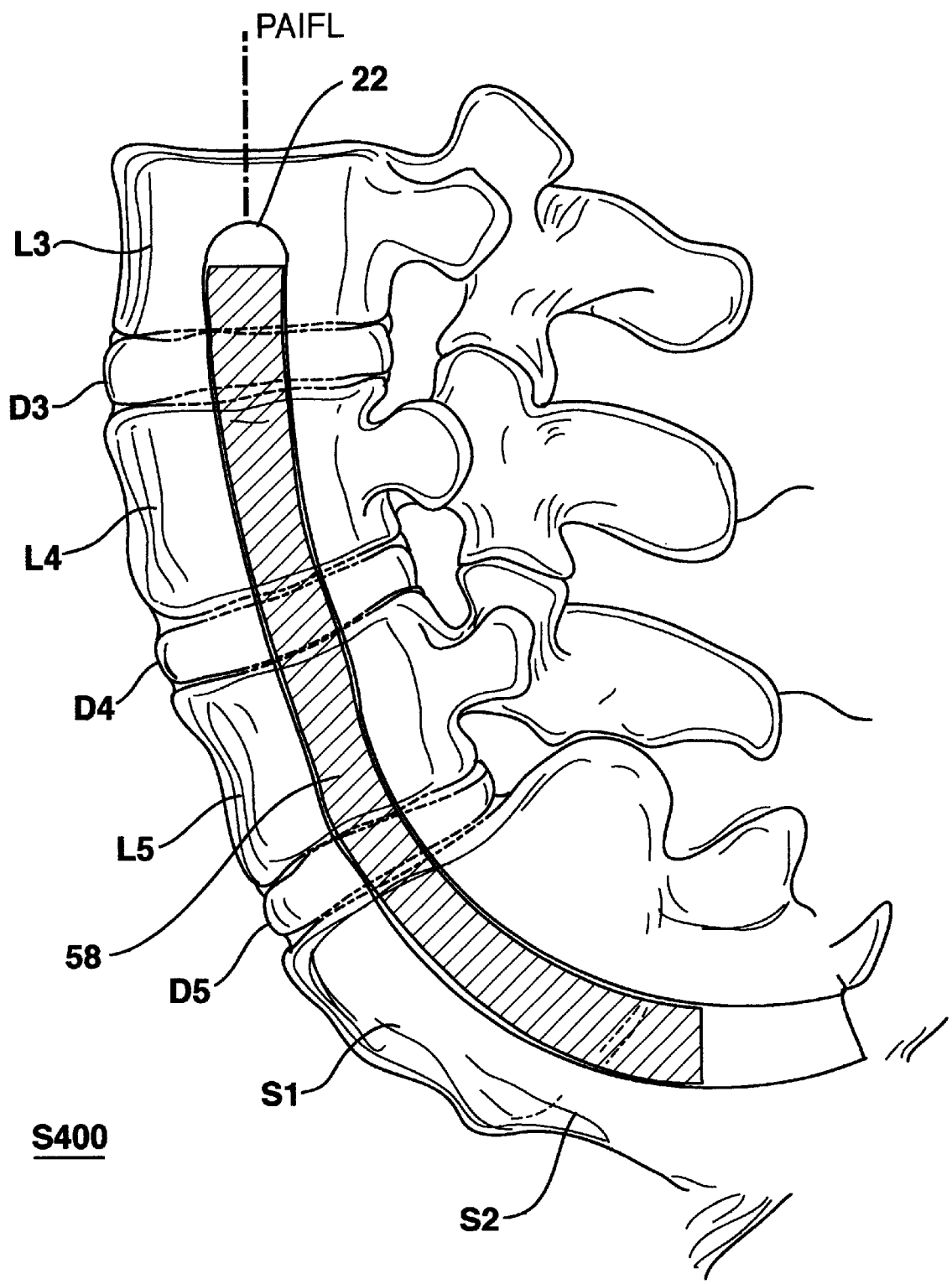
FIG. 11 illustrates the location of a curved posterior TASIF spinal implant of any of the types envisaged by the invention inserted into a curved posterior TASIF axial bore following the curvature of the spine and the visualized, curved PAIFL.

The surgical procedure of step S400 for implanting a curved TASIF spinal implant or rod 58 using an assembly of a spinal implant and a mechanism for implanting or inserting the same in the curved posterior TASIF axial bore is completed as depicted in FIG. 11. A preformed curved TASIF spinal implant or rod 58 can be formed with a spinal implant or rod body having an axial curvature and diameter that is correlated to the diameter and curvature of the curved, posterior TASIF axial bore 22 to provide for a tight fit. The rod body can be hollow, having a rod lumen extending between rod body proximal and distal ends enabling advancement of the rod body over a previously placed guidewire extending into the TASIF axial bore 22, or it can solid and be placed without a guidewire. If present, the rod lumen can be filled with bone fragments retained from drilling posterior TASIF axial bore 22.

In general, the curved TASIF spinal implant or rod 58 is attached at its threaded proximal end 106 to rod 104 and advanced cephalad into the posterior TASIF axial bore 22 until the distal end of rod 58 is fully seated at the cephalad end of the TASIF axial bore 22. The handle 104 is unscrewed from the threads 106 and the remaining insertion tools are withdrawn. The proximal end of the posterior TASIF axial bore 22 is then preferably plugged with bone fragments retained from drilling the posterior TASIF axial bore 22 and bone cement. The laminectomy 14 is repaired, and the posterior tract 18 and skin incision are closed.

If a shape memory or superelastic alloy is employed to form the curved TASIF spinal implant or rod 58 as shown in FIG. 12, it may be inserted with a curved shape corresponding to the TASIF axial bore curvature following the PAIFL. A curved shape shown in broken lines is assumed or can be imparted in a more malleable state when the curved TASIF spinal implant or rod 58 is cooled below or heated above a shape transition temperature lower or higher than body temperature. The curved TASIF spinal implant or rod 58 implanted in the posterior TASIF axial bore 22 can be designed to curve or straighten within the posterior TASIF axial bore 22 as it reaches body temperature from cooler room temperature. After the curved TASIF spinal implant or rod 58 is implanted in the posterior TASIF axial bore 22 (using a spinal implant insertion handle 104 in FIGS. 12 and 13 or a pushing tool), it straightens in the direction of arrow 154 or curves even more in the direction of arrow 156 within the posterior TASIF axial bore as it warms or cools to body temperature. The body temperature shape exerts lateral forces against the bore side wall that causes the curved TASIF spinal implant or rod 58 to be retained therein. The body temperature curvature may also be selected to urge the L4 and L5 vertebrae into a more physiologic or therapeutic alignment. Alternatively, the curved TASIF spinal implant or rod 58 implanted in the posterior TASIF axial bore 22 can be designed to curve even more in the direction of arrow 156 within the posterior TASIF axial bore as it reaches body temperature. In all cases, the curved TASIF spinal implant or rod 58 becomes more rigid at body temperature than when it is at the implantation temperature.

Regardless of the materials used, the curved TASIF spinal implant or rod 58 can also be provided with retention mechanisms including surface roughness, hooks, barbs, screw threads, porous side walls, and the like, alone or in combination, to engage the TASIF axial bore 22 along its length and to encourage bone growth that aids in fixation. Various examples of retention mechanisms are described further below in reference to FIGS. 20–25. As noted above, bone growth encouraging materials including bone fragments harvested from the patient, hydroxylapatite, or bone morphogenic protein (BMP) or the like can be implanted with the spinal implant 58. A bone cement, e.g. polymethylmethacrylate (PMMA) can also be employed to cement the curved TASIF spinal implant or rod 58 into place in the posterior TASIF axial bore 22 along its length.

Anterior TASIF Axial Bore Spinal Implant Implantation:

The anterior TASIF axial bore spinal implant can be curved as shown in FIG. 12 to be inserted into a curved anterior TASIF axial bore or can be straighter as shown by the anterior TASIF axial bore spinal implant 102 of FIG. 13. The implantation of a relatively straight anterior TASIF spinal implant 102 in a straight anterior TASIF axial bore 152 of the type depicted in the assembly 100 of FIG. 13 is described as follows in relation to exemplary procedure steps S200 –S400 of FIG. 6 and the tools depicted in FIGS. 14–18. FIG. 19 depicts a curved TASIF spinal implant or rod 58 implanted into a curved anterior axial bore 152' tracking a curved AAIFL.

Various methods and surgical tool sets for forming an anterior percutaneous pathway and percutaneous tract are set forth in the above-referenced 222 application and summarized as follows. The anterior percutaneous pathway formed in step S100 is preferably accomplished employing an elongated guide member that is introduced through the skin incision and advanced against the anterior sacrum through the presacral space until the guide member distal end is located at the anterior target point. The posterior viscera are pushed aside as the guide member is advanced through presacral space and axially aligned with the AAIFL at the anterior target point of the anterior sacral surface.

The guide member may take a variety of forms including a blunt tip rod or a guide assembly of an inner occluder and an outer tubular member fitted together having a tubular member lumen receiving the occluder. The occluder may take the form of a solid body member, e.g., an obdurator, a stylet, a guidewire or the like, and the tubular member may take the form of a needle, a trocar, a catheter or the like. Either or both of the inner occluder and outer tubular member may comprise distal fixation mechanisms that enable fixation to the sacral vertebral surface at the anterior target point and/or at the cephalad end of a pilot hole for each such anterior TASIF bore optionally bored along or parallel with the visualized AAIFL. The occluder can be employed to blunt the tip of the outer tubular member during introduction to the anterior target point, if the outer tubular member comprises a distal tip fixation mechanism that would otherwise prematurely engage the sacral bone. Or the occluder can have a distal tip fixation mechanism and be retracted within the outer tubular member to prevent its premature attachment to sacral bone during introduction to the anterior target point.

In its simplest forms, the anterior, presacral, percutaneous tract formed in step S100 can take the form of the lumen of the outer tubular member upon removal of the occluder or a tube inserted alongside the guide member. The anterior percutaneous pathway can be expanded to form the anterior, presacral, percutaneous tract through the patient's anterior presacral space having a tract axis aligned with the visualized AAIFL to provide working space and exposure of the sacrum. In one embodiment, a guidewire having a distal fixation mechanism (which may comprise the occluder) provides the anterior, presacral, percutaneous tract for over-the-wire passage extending from the skin incision to the targe act and aligned with the visualized AAIFL. In further embodiments, the lumen of a further tract sheath introduced through the percutaneous pathway, e.g., over the guidewire or after removal of the guidewire, provides a percutaneous tract for over the wire passage extending from the skin incision to the target point and aligned with the visualized AAIFL. The further tract sheath preferably has a distal tract sheath fixation mechanism and configuration that enables alignment and attachment to the anterior sacral bone at the anterior target point to maintain the tract sheath lumen aligned axially with a the visualized AAIFL.

The tissue surrounding the skin incision and the anterior, presacral, percutaneous pathway through the presacral space may optionally be dilated to form an enlarged diameter presacral, percutaneous tract surrounding a guidewire or tubular member and or to accommodate the insertion of a tract sheath over the guidewire. Dilation can be accomplished manually or by use of one or more dilator or dilatation balloon catheter or any tubular device fitted over a previously extended tubular member or guidewire.

Additionally, a pilot hole can be bored in axial alignment or parallel with the visualized AAIFL by a boring tool introduced through the outer tubular member lumen for each such anterior TASIF bore bored along or parallel with the visualized AAIFL. The guidewire distal end fixation mechanism is then affixed to vertebral bone at the cephalad end of the pilot hole to provide the percutaneous tract for guiding a drill or other instrument to form the anterior TASIF bore or conduct discectomies or disc or vertebral bone augmentation.

Figure 14:
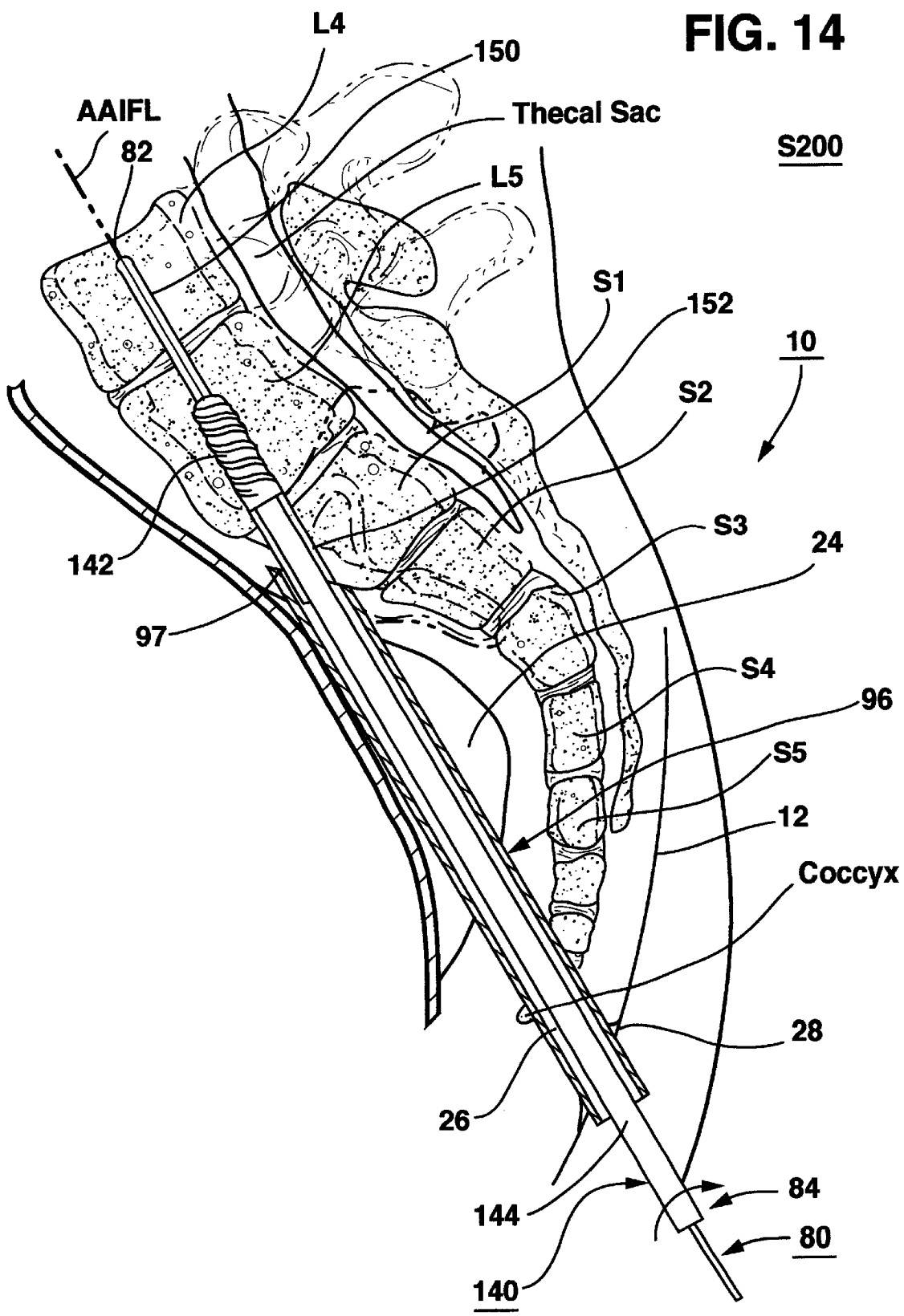
FIG. 14 illustrates one exemplary method of steps S100 and S200 of FIG. 6 for providing an anterior percutaneous tract to the anterior target point of the anterior sacrum aligned with the AAIFL and one manner of forming an anterior TASIF axial bore through sacral and lumbar vertebrae and intervening discs axially aligned with the visualized AAIFL of FIGS. 1 and 2.

In the anterior TASIF approach, the junction of S1 and S2 is located through a presacral, percutaneous tract posterior to the rectum and extending from a skin incision adjacent the coccyx using a guide member or assembly as described above. FIG. 14 is an exemplary illustration of certain of the above-described techniques for forming the anterior percutaneous tract 26 and inserting a percutaneous tract sheath 96 and guidewire 80 therethrough. One or more relatively straight anterior TASIF axial bore 152 into at least L5 can then be formed in the vertebral column accessed via the anterior, presacral, percutaneous tract to receive a TASIF spinal implant and/or interventional tools inserted through the anterior, presacral, percutaneous tract. However, a curved anterior TASIF axial bore 152' following a visualized, curved, AAIFL extending therethrough as depicted in FIG. 19 can be formed to follow the curvature of the vertebrae L4, L3, et seq. in the cephalad direction using the drill 40 of FIG. 9 or drill 40' of FIG. 10.

FIG. 14 also depicts further steps of forming a pilot hole 150 and use of the guidewire 80 and a drill bit 140 attached to a drill motor (not shown) to form an anterior TASIF axial bore 152 falling within step S200. In this illustrated example of one way to form an anterior TASIF axial bore, the pilot hole 150 is formed using a smaller diameter drill bit (not shown) extended through a further smaller diameter tract sheath attached at its distal end to the anterior sacrum at the anterior target point (not shown). Or a hollow lumen pilot hole drill bit can be advanced over the guidewire 80 attached at its distal end screw-in tip 82 to the anterior sacrum at the anterior target point and rotated to drill or bore the pilot hole 150.

Then, the guidewire 80 is attached at its distal end screw-in tip 82 to the cephalad end of the pilot hole 150, and, optionally, the enlarged diameter tract sheath 96 is placed as shown with its beveled distal end 97 abutting the angled surface of the anterior sacrum. The tract sheath 96 and/or guidewire 80 are aligned axially with the AAIFL, and the enlarging tool 140 is used to enlarge the pilot hole diameter and form the larger diameter anterior TASIF axial bore 152. The larger diameter enlarging tool 140, e.g., a drill bit, ranguer or tap, used in step S200 and shown in FIG. 14 preferably has a 10.0 mm diameter distal head 142 mounted to the distal end of a tool shaft 144. An enlarging tool lumen 146 extends between the proximal and distal ends of the enlarging tool 140 and enables the enlarging tool 140 to be advanced over the guidewire 80 to position the distal head 142 at the caudal end of the pilot hole 150. A hand operable knob or handle (not shown) may be provided at the proximal end of the enlarging tool shaft 144 so that shaft 144 and distal head 142 can be rotated manually to bore or ream or tap out a larger diameter anterior TASIF axial bore 152 as shown in FIG. 20. Or the enlarging tool shaft proximal end may be coupled to a drill motor to rotate distal head 142 in the manner of a drill bit. The enlarging tool 140 is then withdrawn through the anterior TASIF axial bore 152 and the anterior tract 26 over the guidewire 80. The guidewire screw-in tip 82 can then be unscrewed from the vertebral bone at the cephalad end of the anterior TASIF axial bore 152 as described above, if it is not needed to perform steps S300 and S400. The above-described procedure may be repeated to form two or more parallel anterior TASIF axial bores 152.

It will be understood that the anterior TASIF axial bore(s) 152 can be formed in a simpler manner in a single step without first forming a pilot hole 150 or using the above-described guidewire 80 or tract sheathes. No matter how it is formed, the longitudinal, anterior TASIF axial bore(s) 152 or 152' that is formed in steps S100 and S200 of FIG. 6 as described above in reference to FIG. 14 starts in the sacrum at the anterior target point and extends upwardly or cephalad through the vertebral body of S1 or S2 and through the cephalad vertebral bodies including L5 and L4 and the intervening discs denoted D4 and D5 in FIG. 1. Discs D4 and D5 are usually damaged or have degenerated between lumbar spine vertebrae and cause the pain experienced by patients requiring intervention and fusion of the vertebrae. A visual inspection, discectomy and/or disc augmentation and/ or vertebroblasty may be performed pursuant to step S300 of FIG. 6 through the axially aligned anterior TASIF axial bore 152 and anterior tract 26 to relieve the patient's symptoms and aid in the fusion achieved by the spinal implant or rod 152.

Figure 15:
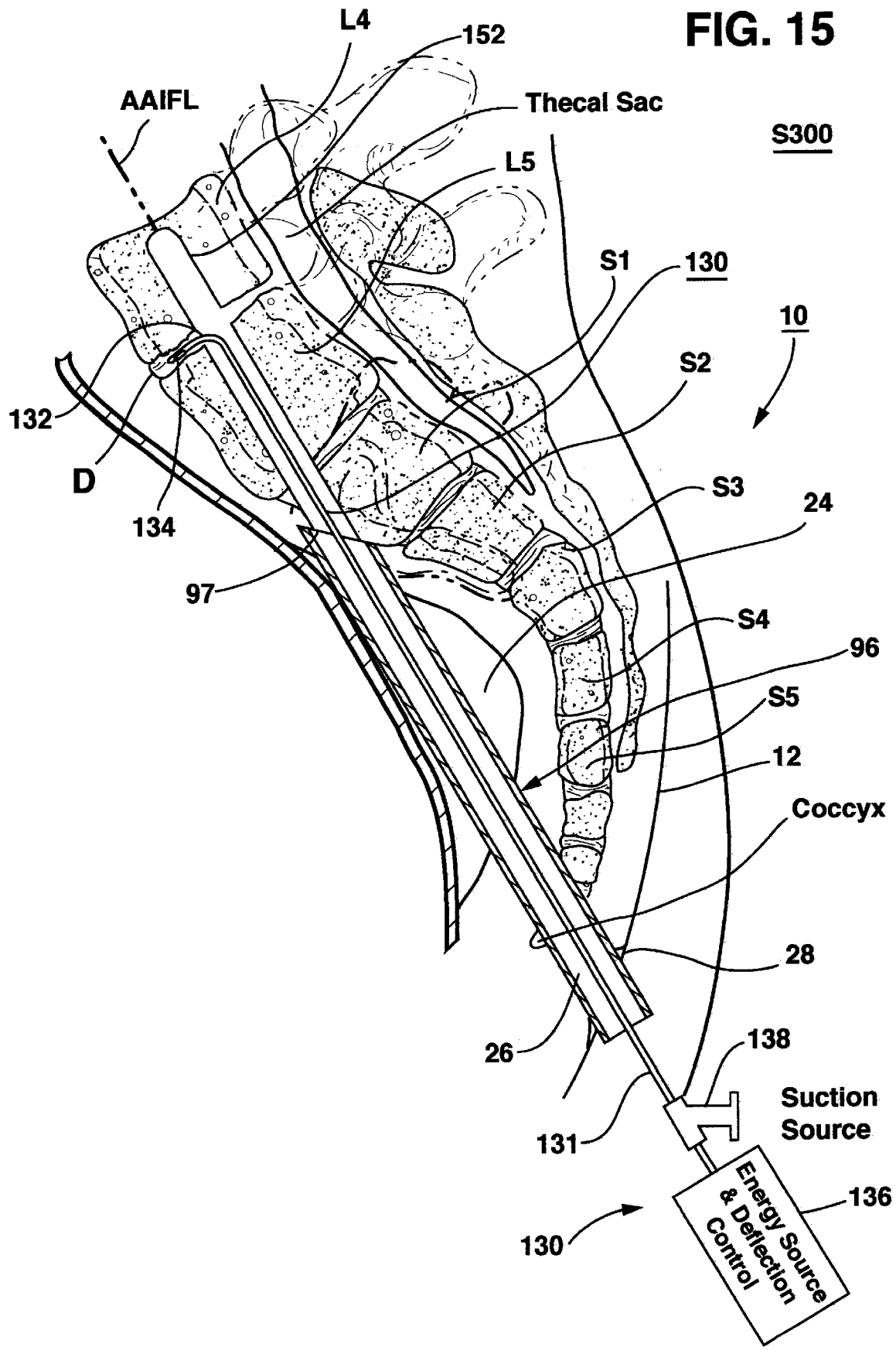
FIG. 15 illustrates one manner of performing a discectomy through the TASIF axial bore and anterior tract in accordance with step S300 of FIG. 6.

FIG. 15 depicts a insertion of a motor driven discectomy tool 130 through the axially aligned anterior tract 26 and anterior TASIF axial bore 152 or 152' and then laterally into D4 to mechanically fragment and remove the disc material pursuant to step S300 of FIG. 6. It will be understood that this illustrated discectomy procedure can also be practiced through the posterior TASIF bore 22. Moreover, the illustrated discectomy procedure may be performed through the pilot hole formed in step S100 of FIG. 6 and illustrated in FIG. 15 both in the anterior and the posterior TASIF procedure.

The discectomy tool 130 is formed like a flexible atherectomy catheter for fragmenting and removing obstructions in blood vessels using a cutting head 134 to fragment the disc material and aspiration or water flushing to remove the fragments from the disc space. The cutting mechanism 134 is mounted into a deflectable or steerable distal end section 132 that may be angularly deflected using a pull wire within a pull wire lumen of the elongated, flexible, discectomy tool body 131 and a proximal pull wire control of a proximal guiding and cutting mechanism 134 coupled thereto as described above in reference to deflection mechanism of the drill 40 of FIG. 9. The cutting mechanism 134 may comprise any of the known types, e.g., rotating wires, cutting blades, screws, bits, or the like, or using laser energy or ultrasonic energy or water jets or the like. The cutting mechanism 134 is powered by an energy source within energy source and direction control 136 e.g., a drive motor for rotating a mechanical cutting head, or a source of energy for operating the ultrasonic generator or laser or pressurized fluid. The cutting mechanism 134 is controlled by a deflection control within energy source and deflection control 136 for operating the pull wire or the like. Preferably an aspiration lumen is included within the discectomy sheath body 131 with a distal opening adjacent to the cutting head 134 and terminating proximally at a side suction port 138 adapted to be coupled to a source of suction to aspirate the fragments of the disc.

Figure 16:
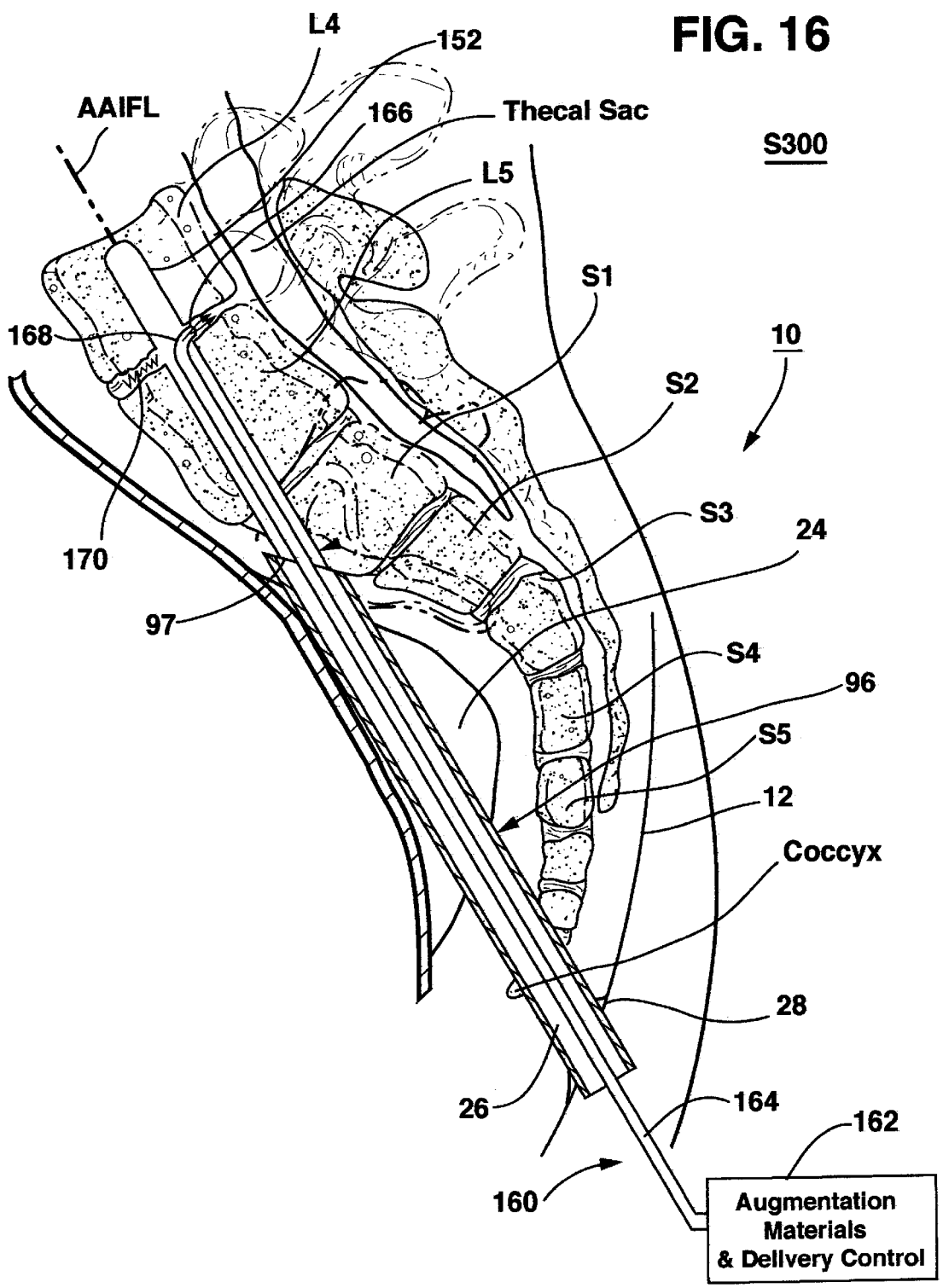
FIG. 16 illustrates one manner of performing a disc augmentation through the TASIF axial bore and anterior tract in accordance with step S300 of FIG. 6.

FIG. 16 depicts a disc augmentation tool 160 having a proximal source of augmentation materials 162 coupled to an augmentation tool shaft 164 for delivering augmentation materials to distal exit port 166 in a deflectable distal section 168 of the augmentation tool shaft 164. The augmentation procedure is illustrated in FIG. 22 in the context of employing the anterior TASIF axial bore 152 or pilot hole 150, but FIG. 16 is intended to convey how the same procedure would be employed using augmentation tool 160 to augment discs accessed via the posterior TASIF axial bore or pilot hole. The disc augmentation procedure employs augmentation materials 170, e.g., a solid particulate material or a polymer or gel introduced in a fluid form to solidify in situ to provide support between the opposed vertebral bodies. One or more self-contained inflatable sac may be delivered into each disc space created in a preceding discectomy or discoscopy and then filled with the disc augmentation materials through the distal exit port 166.

Or, the disc augmentation materials can be pumped or otherwise delivered directly into each disc space through the distal exit port 166. Alternatively, the disc augmentation materials can be pumped or otherwise delivered directly into the pilot hole 150 of FIG. 14 to fill the disc spaces through it if the disc augmentation procedure employs the pilot hole 150. The excess disc augmentation materials can be removed form the pilot hole when it is enlarged by the enlarging tool 140 as shown in FIG. 14.

If the pilot hole 150 is used, then the pilot hole 150 may be drilled in the cephalad direction to access disc D5, whereupon a discectomy and disc augmentation procedure may be performed as described above. Then, the pilot hole 150 may be advanced to access disc D4, and the discectomy and disc augmentation procedure may be performed as described above.

The vertebroblasty procedure of step S300 may also be performed via the posterior and anterior pilot holes or TASIF axial bores using an elongated catheter having a deflectable distal end portion and exit port. The distal end portion can be aimed at the side wall of the posterior and anterior pilot holes or TASIF axial bores at selected points and pushed into fractured regions of the vertebral bodies since the vertebral bodies of L4 and L5, for example, are already penetrated by the posterior and anterior pilot holes or TASIF axial bores. It is possible to then pump or otherwise deliver reinforcing materials therein to solidify therein in situ.

Figure 17:
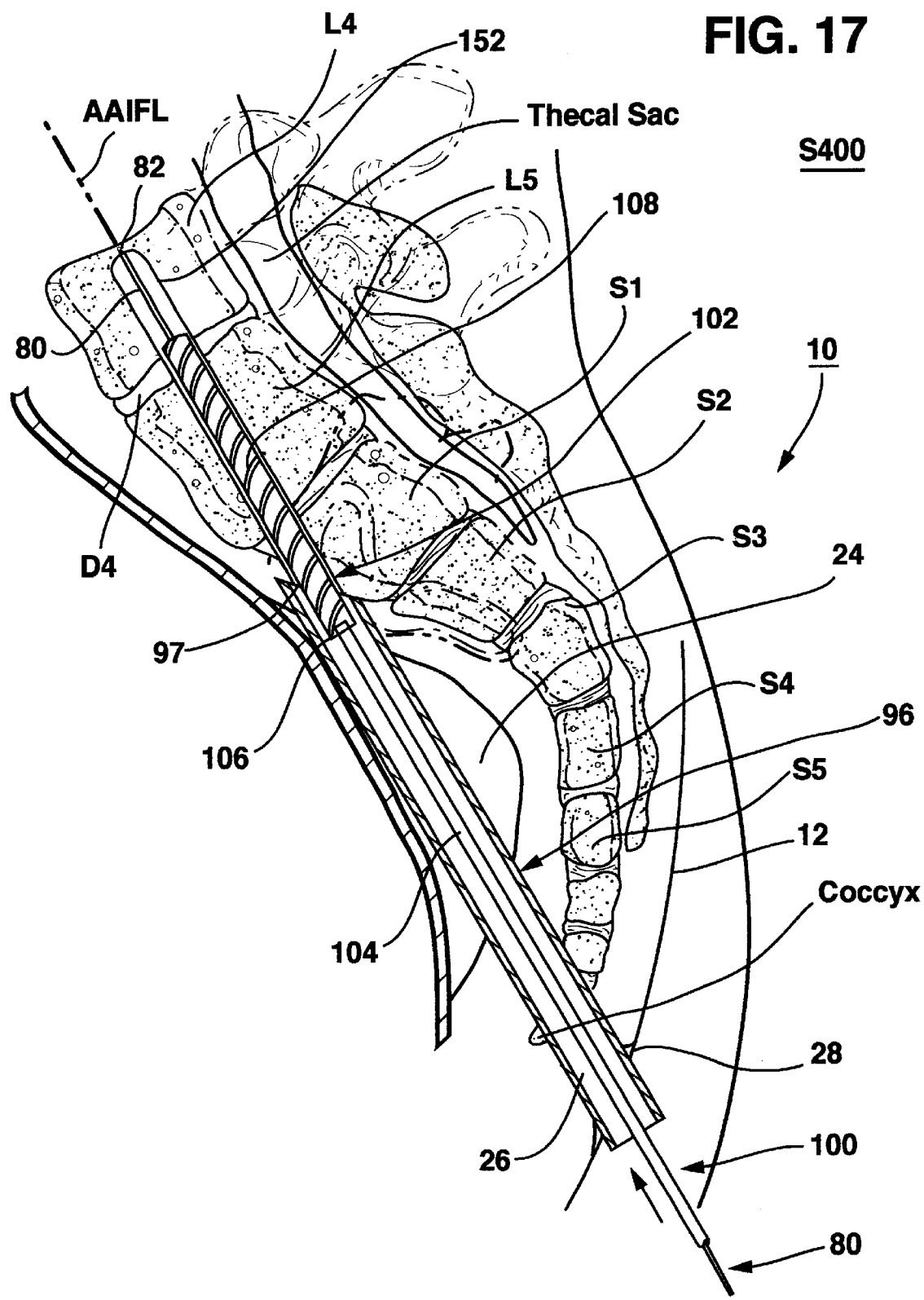
FIG. 17 illustrates the insertion of a relatively straight anterior TASIF spinal implant of any of the types envisaged by the invention into a relatively straight anterior TASIF axial bore in accordance with step S400 of FIG. 6.

Step S400 of FIG. 6 is then performed after step S200 and any of the procedures of step S300 are completed. FIG. 17 illustrates the performance of step S400 using the spinal implant assembly 100' of FIG. 13 including an anterior TASIF spinal implant or rod 102 being inserted into the relatively straight anterior TASIF axial bore 152. The anterior spinal implant assembly 100' of FIG. 13 comprises the anterior TASIF spinal implant or rod 102 coupled to a spinal implant insertion handle 104 through an attachment and detachment screw thread 106. The anterior TASIF spinal implant or rod 58 and the insertion handle 104 can be formed with a rod lumen 103 and handle lumen 105, respectively, to allow advancement of the spinal implant assembly over the previously placed guidewire 80 as shown in FIG. 17. Or the spinal assembly 100 can be formed without such lumens and can be placed without the guidewire 80 after the guidewire is withdrawn from the anterior TASIF axial bore 152. The spinal implant or rod 102 have a surface treatment or retention mechanism of one of the types described below in reference to FIGS. 20–25 and equivalents thereof alone or in combination.

In general, the anterior TASIF spinal implant or rod 102 is advanced cephalad over the guidewire 80 or after the guidewire 80 is withdrawn until its distal end is fully seated at the cephalad end of the anterior TASIF axial bore 152. The handle 104 is detached and the remaining insertion tools and the anterior tract sheath 96 are withdrawn. The proximal end of the anterior TASIF axial bore 152 is plugged with bone fragments retained from drilling the anterior pilot hole 150 and anterior TASIF axial bore 152 and bone cement, and the skin incision 28 are closed.

Figure 18:
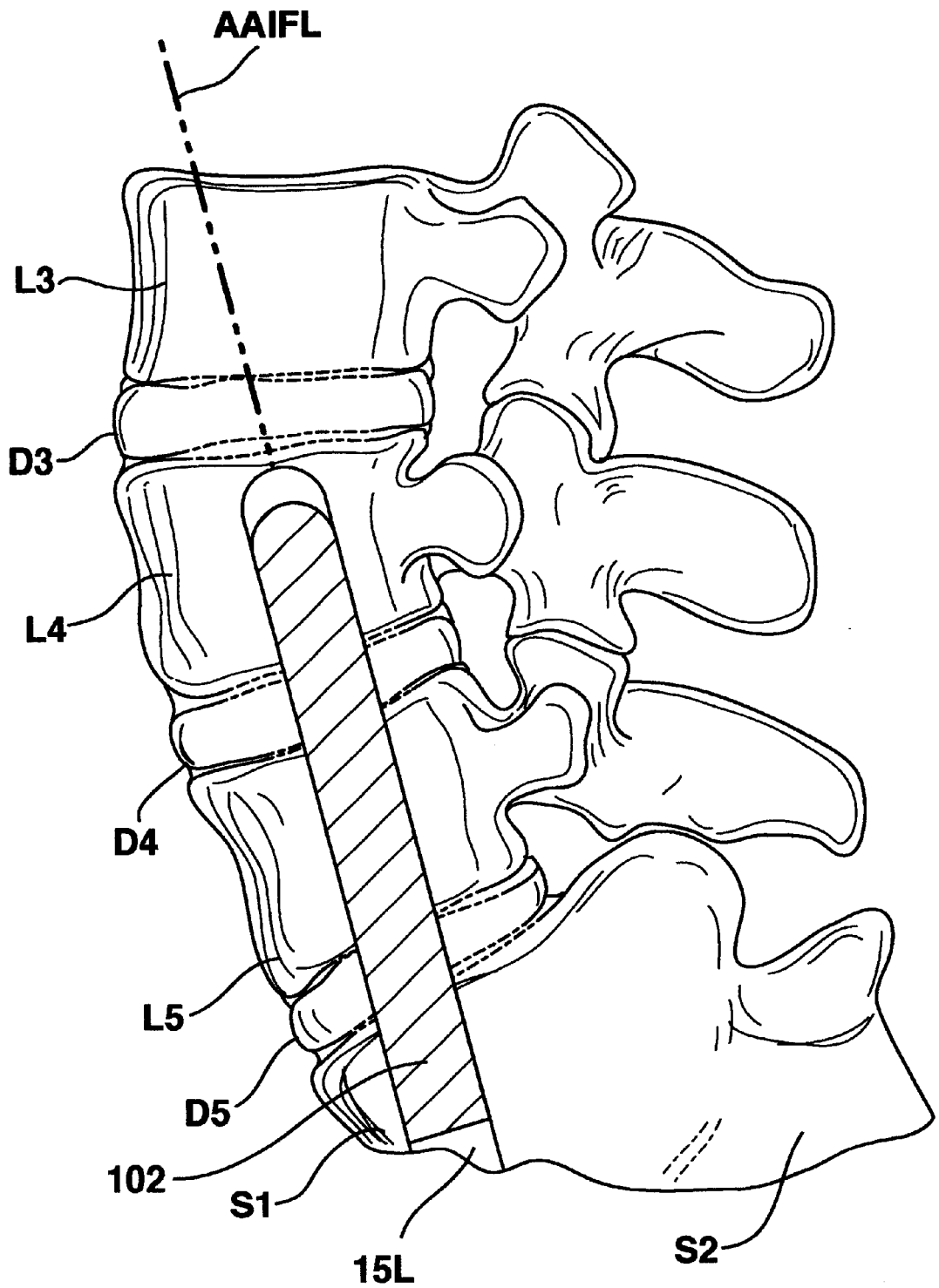
FIG. 18 illustrates the location of the relatively straight anterior TASIF spinal implant of any of the types envisaged by the invention inserted into a relatively straight anterior TASIF axial bore.
Figure 19:
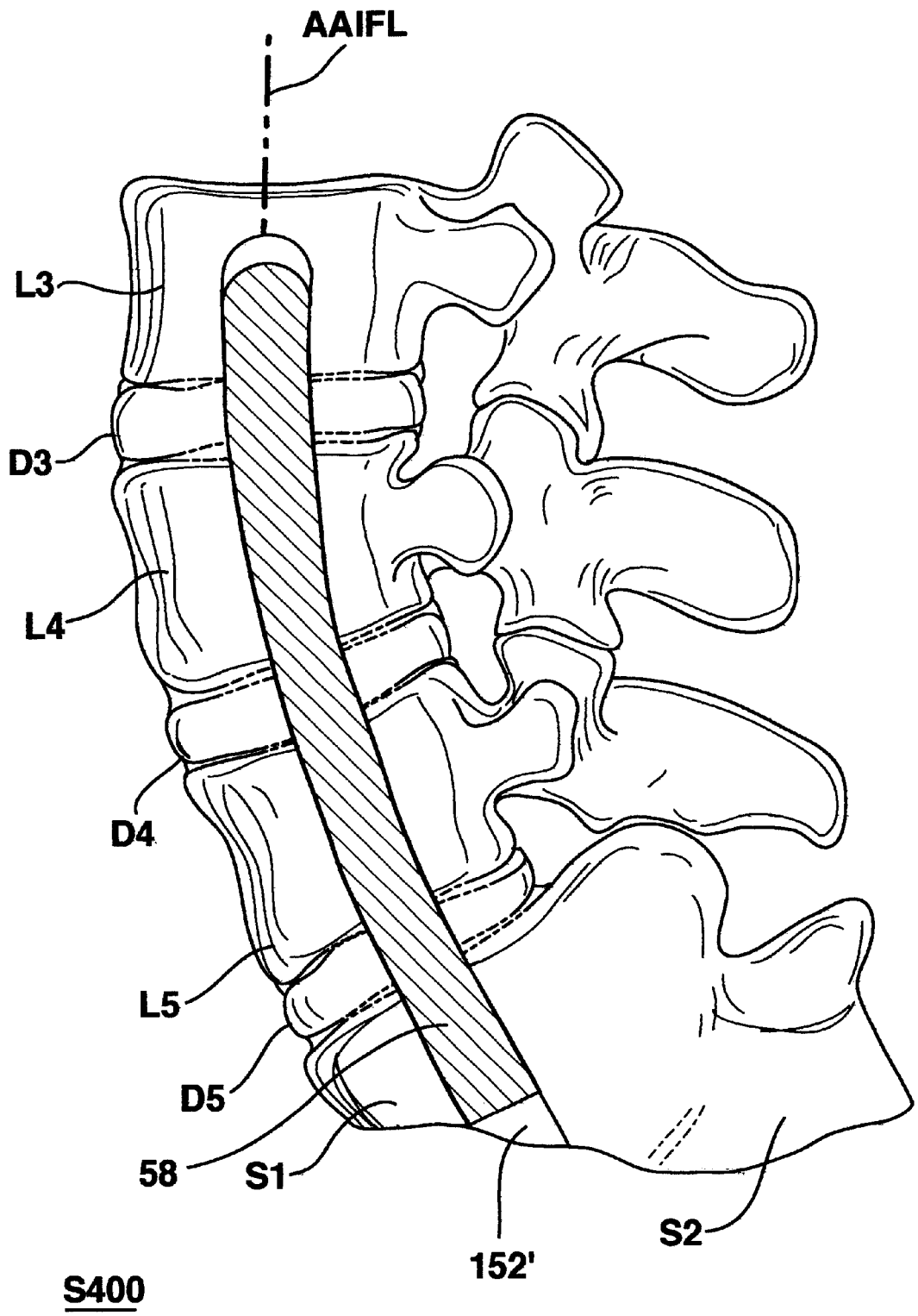
FIG. 19 illustrates the location of a curved anterior TASIF spinal implant of any of the types envisaged by the invention inserted into a curved anterior TASIF axial bore following the curvature of the spine.

FIG. 18 depicts the final disposition of a generic form of the relatively straight anterior TASIF spinal implant or rod 102, including the embodiments described above in reference to FIG. 13 and in the following description of further alternative embodiments. If a shape memory or superelastic alloy is employed to form the anterior TASIF spinal implant or rod 102, its initial shape upon insertion is relatively straight as shown in solid lines in FIG. 13 so that it can be inserted in the anterior TASIF axial bore 152. After the straight anterior TASIF spinal implant or rod 102 is implanted as shown in FIG. 17, the rod body curves in the direction of arrow 154 within the anterior TASIF axial bore 152 and becomes more rigid as it reaches body temperature as shown by the broken line position of FIG. 13.

FIG. 19 depicts the final disposition of a generic form of the curved anterior TASIF spinal implant or rod 52, including the embodiments described above and in the following description of further alternative embodiments. If a shape memory or superelastic alloy is employed to form the curved TASIF spinal implant or rod 58, its initial shape upon insertion is curved as shown in solid lines in FIG. 12 so that it can be inserted into the curved anterior TASIF axial bore 152'.

In both cases illustrated in FIGS. 12 and 13, the broken line, body temperature shapes exert lateral forces against the TASIF axial bore side wall that causes the curved and anterior spinal implants or rods 58 and 102 to be retained therein. The body temperature rod curvature may also be selected to impart a physiologic or therapeutic biasing curvature to the vertebrae that they pass through. Thus, corrective forces can be applied laterally to maintain a corrected curvature of the spine in the case of above listed types of spinal column disorders.

Regardless of the materials used, the curved TASIF spinal implant or rod 58 or relatively straight anterior TASIF spinal implant or rod 102 can also be provided with retention mechanisms including surface roughness, hooks, barbs, screw threads, porous side walls, and the like, alone or in combination, to engage the anterior TASIF axial bore 152 along its length and to encourage bone growth that aids in fixation. Various examples of retention mechanisms are described further below in reference to FIGS. 20–26. As noted above, bone growth encouraging materials including bone fragments harvested from the patient, hydroxylapatite, or bone morphogenic protein (BMP) or the like can be implanted with the spinal implant 58 or 102. A bone cement, e.g. polymethylmethacrylate (PMMA), can also be employed to cement the curved TASIF spinal implant or rod 58 into place in the posterior TASIF axial bore 22 along its length.

Further Spinal Implant Embodiments

Further embodiments of posterior and anterior spinal implants or rods of the present invention adapted to be fitted into the posterior and anterior TASIF axial bores 22 and 152, 152' and having specific fixation mechanisms are depicted in FIGS. 21–26. Certain of the illustrated types of posterior and anterior spinal implants of FIGS. 21–26 can be curved or straight. The illustrated fixation mechanisms can be used alone or in combination and can extend the length of the spinal implant body or be restricted to caudal or cephalad portions of the spinal implant body that engage the caudal or cephalad vertebral bodies that the axial bore extends through. Two or more such spinal implants of FIGS. 21–26 can be implanted in the two or more posterior or anterior TASIF axial bores $22_1$, $152_1/22_2$, $152_2$ of FIG. 5, for example.

FIG. 20 illustrates a further embodiment of a straight anterior or curved posterior or anterior TASIF spinal implant 310 having a plurality of elongated flutes 312 extending along the outer surface of the spinal implant body 314 through the full length or one or more portion of the length of the spinal implant body 314. The implant system 300 also includes an insertion tool 320 optionally having a distal end 322 releasably engaging the proximal end opening 316 of the spinal implant body 314 for pushing the same into the anterior or posterior TASIF axial bore. If the outer diameter of the spinal implant body 314 measured between diametrically opposed flutes 312 is greater than the diameter of the axial bore 22 or 152 (or parallel axial bores $22_1$, $152_1/22_2$, $152_2$ depicted in FIG. 5), then the flutes 312 bite into the vertebral bone traversed by the axial bore 22, 152. However, the outer diameter measured across the diametrically opposed flutes 312 can be equal to or smaller than the diameter of the axial bore 22 or 152 (or parallel axial bores 22₁, 152₁/22₂, 152₂ depicted in FIG. 5), so that bone cement of growth material can be inserted into the bore and distributed about the flutes during the implantation of the TASIF spinal implant 310 into the bore. A hollow lumen 318 extending through the spinal implant body 314 is depicted, but the spinal implant body 314 can be solid and can include a pointed distal end as in FIG. 22.

Although elongated continuous flutes 312 are depicted in this embodiment, it will be understood that they may be interrupted periodically. Moreover, the interruptions can be so closely spaced as to form a knurled outer surface pattern for bone ingrowth.

FIG. 21 illustrates a further embodiment of a straight anterior or curved posterior or anterior TASIF spinal implant 410 having a plurality of barbs 412 distributed along the outer surface of the spinal implant body 414 through the full length or one or more portion of the length of the spinal implant body 414. The implant system 400 also includes an insertion tool 420 optionally having a distal end 422 releasably engaging the proximal end opening 416 of the spinal implant body 414 for pushing the same into the anterior or posterior TASIF axial bore. If the outer diameter of the spinal implant body measured between diametrically opposed barb tips of the barbs 412 is greater than the diameter of the axial bore 22 or 152 (or parallel axial bores 22₁, 152₁/22₂, 152₂ depicted in FIG. 5), then the he barbs 412 bite into the vertebral bone traversed by the axial bore 22, 152. However, the outer diameter measured across the barb tips can be equal to or smaller than the diameter of the axial bore 22 or 152 (or parallel axial bores 221, 152₁/22₂, 152₂ depicted in FIG. 5), so that bone cement of growth material can be inserted into the bore and distributed about the flutes during the implantation of the TASIF spinal implant 410 into the bore. A hollow lumen 418 extending through the spinal implant body 414 is depicted, but the spinal implant body 414 can be solid and can include a pointed distal end.

FIG. 22 illustrates a further embodiment of a straight anterior or curved posterior or anterior TASIF spinal implant 510 having a plurality of flanges 512 distributed along the outer surface of the spinal implant body 514 through the full length or one or more portion of the length of the spinal implant body 514. The implant system 500 also includes an insertion tool 520 optionally having a distal end 522 releasably engaging the proximal end opening 516 of the spinal implant body 514 for pushing the same into the anterior or posterior TASIF axial bore. The outer diameter of the spinal implant body 514 measured across the flange edges can be equal to or smaller than the diameter of the axial bore 22 or 152 (or parallel axial bores 22₁, 152₁/22₂, 152₂ depicted in FIG. 5), so that bone cement or bone growth material can be inserted into the bore and distributed about the flanges during the implantation of the TASIF spinal implant 410 into the bore. The spinal implant body 514 is illustrated as solid and including a pointed distal end 530, but the spinal implant body can be formed with a hollow lumen extending the length of the spinal implant body 514.

Figure 23:
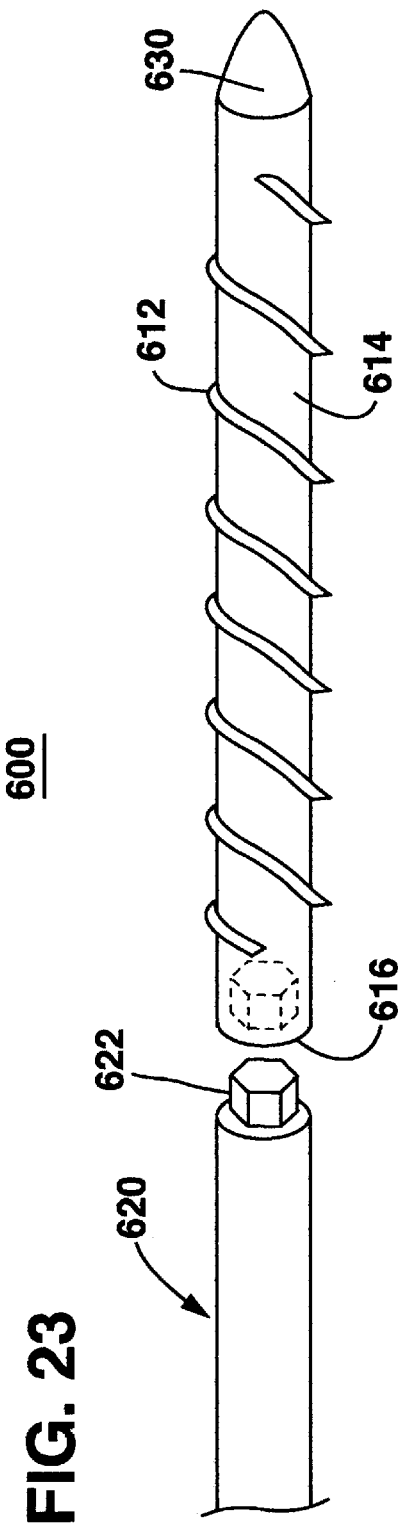
FIG. 23 illustrates a further embodiment of a straight anterior TASIF is spinal implant having a spiral screw thread around the spinal implant body surface and an insertion tool for inserting the same into a relatively straight anterior TASIF axial bore.

FIG. 23 illustrates a further embodiment of a TASIF spinal implant 602 having a spiral screw thread 612 around the surface or the spinal implant body 614 and an insertion tool 620 for inserting the same into a relatively straight anterior TASIF axial bore 152. The insertion tool 620 has a distal end 622 having a hexagonal wrench configuration, for example, for releasably engaging the proximal end opening 616 of the spinal implant body 614 for rotating the same to advance it into the straight anterior TASIF axial bore. As the spinal implant body 614 is rotated, the screw thread 612 bites into the vertebral bone traversed by the axial bore 152 or bores 152₁, 152₂ as the or through bone fragments inserted into a bore having a diameter exceeding the diameter of the spinal implant body. The spinal implant body 614 is illustrated as solid and including a pointed distal end 630, but the spinal implant body 614 can be formed with a hollow lumen extending the length of the spinal implant body 614.

The screw thread 612 can be provided on a curved anterior or posterior TASIF spinal implant that has an outer diameter that is smaller than the bore of the respective curved anterior or posterior TASIF axial bore to allow insertion of the curved spinal implant body into the bore. Then, bone growth about the screw thread 612 provides fixation by engagement with the vertebral bone.

However, if the spinal implant 602 is formed of a shape memory material that is superelastic at the implantation temperature, it can be screwed into a curved axial bore. The superelastic implant body can conform with the curvature of a curved axial bore as the implant body is rotated from its proximal end to enable the screw threads to track a spiral cut into the bore wall of the curved axial bore.

Figure 24:
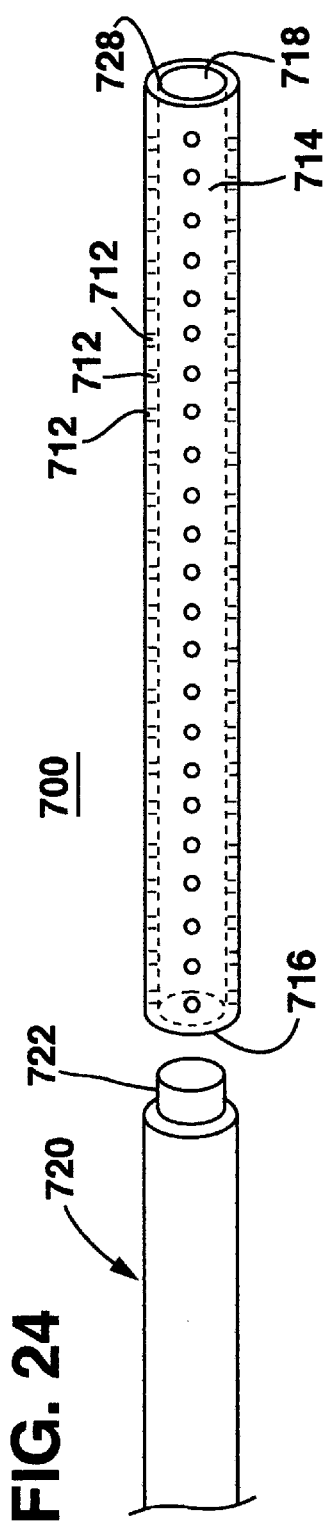
FIG. 24 illustrates a further embodiment of a straight anterior or curved posterior or anterior TASIF spinal implant having a hollow lumen and porous side wall and an insertion tool for inserting the same into a curved anterior or posterior TASIF axial bore.

FIG. 24 illustrates a further embodiment of a straight anterior or curved posterior or anterior TASIF spinal implant 702 having a hollow lumen 718 and a porous side wall 728. The implant system 700 also includes an insertion tool 720 having a distal end 722 releasably engaging the proximal end opening 716 of the spinal implant body 714 for pushing the same into the anterior or posterior TASIF axial bore. The openings or pores 712 can be formed as etched or machined or laser drilled through-holes to the lumen 718 in a tubular pipe-like spinal implant body 714. Or the spinal implant body 714 can be formed of a tubular mesh or lattice. Materials of the type described above for enabling fixation and/or enhancing bone growth can be inserted into the lumen 718 and passed through the pores 718. An open distal end to the hollow lumen 718 extending through the spinal implant body 714 is depicted, but the distal end of the spinal implant body 714 can be closed and can include a pointed distal end. Any of the above-described spinal implants can be modified to include the hollow lumen 718 and the openings or pores 712.

Figure 25:
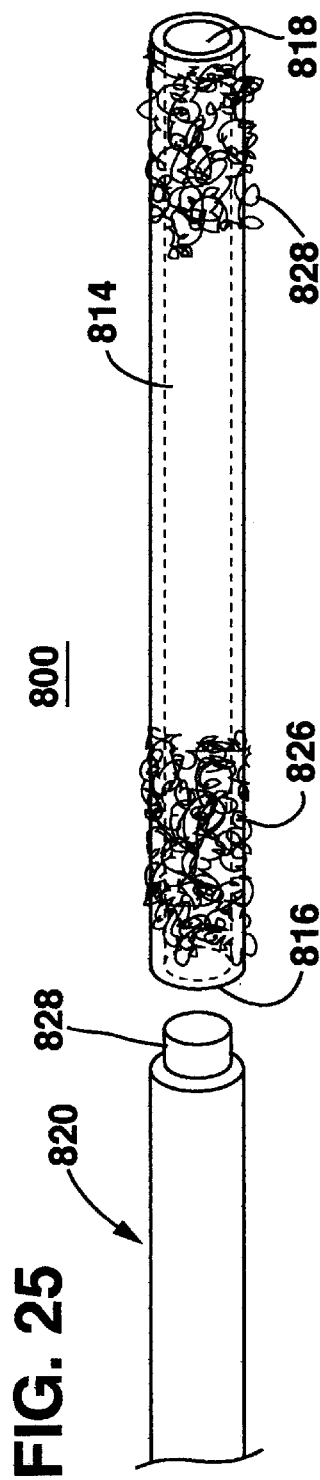
FIG. 25 illustrates a further embodiment of a straight anterior or curved posterior or anterior TASIF spinal implant having a hollow lumen and a surface roughening treatment in caudal and cephalad portions of the spinal implant body and an insertion tool for inserting the same into a curved anterior or posterior TASIF axial bore.

FIG. 25 illustrates a further embodiment of a straight anterior or curved posterior or anterior TASIF spinal implant 802 having a hollow lumen 818 and surface roughening treatments 826 and 828 in caudal and cephalad portions of the spinal implant body 814. The implant system 800 also includes an insertion tool 820 having a distal end 822 releasably engaging the proximal end opening 816 of the spinal implant body 814 for pushing the same into the anterior or posterior TASIF axial bore. The surface roughening treatments 826 and 828 can be formed by scribing, sintering particles to, partially through etching, or otherwise roughening the surface to make it more receptive to bone in-growth in situ. An open distal end to the hollow lumen 818 extending through the spinal implant body 814 is depicted, but the distal end of the spinal implant body 814 can be closed and can include a pointed distal end. The roughened surface treatment can extend the full length of the surface of the spinal implant body 814, and any of the above-described spinal implants can be modified to include the roughened surface treatment.

In certain cases, it may be advantageous to install a spinal implant of one of the above-described types in the cephalad section of the TASIF axial bore to bridge the space labeled D4 between vertebrae L4 and L5 normally occupied by a disc. Then, a second TASIF spinal implant is installed in the caudal section of the same axial bore to bridge the space labeled D5 between vertebrae L5 and sacrum S1 normally occupied by a disc. The discs at D4 and/or D5 may have been removed and/or augmented.

It is expected that the caudal ends of the posterior and anterior TASIF bores would be filled with a material or autologous bone after implantation of any of the above-described spinal implants to close the anterior or posterior sacral surface opening.

Moreover, various materials may be used in the above described anterior and posterior TASIF procedures including: (1) resorbable cement material is a calcium derivative generally composed of hydroxyapatite, orthophosphoric acid, calcium carbonate, and calcium hydroxide formed into a semi-liquid paste with an alkaline solution of sodium hydroxide and water; (2) resorbable cement material is a composition comprising polypropylene fumarate; (3) compositions further comprising calcium salt filler, N-vinyl-2-pyrrolidone, and a peroxide or free radical initiator; and (4) resorbable cement material comprising a mixture of calcium phosphates.

Such materials placed in the TASIF axial bores with the TASIF spinal implants cure therein such that fixation occurs between the spinal implants and adjacent vertebral bone of sufficient strength to withstand physiological loads until fixation occurs by osteogenic growth between the bone and the TASIF spinal implants.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto now known and coming into existence during the term of the patent. Thus, it is expected that various changes, alterations, or modifications may be made to the invention as described herein without departing from the spirit and scope of the invention as defined by the appended claims.

What is claimed is:

1. A method of treating a series of adjacent vertebrae located within a human lumbar and sacral spine having an anterior aspect, a posterior aspect and an axial aspect, the vertebrae separated by intact or damaged spinal discs, the method comprising the steps of:

accessing an anterior sacral position of the anterior surface of a sacral vertebra through pre-sacral space;

boring an anterior axial bore extending along a visualized, axial instrumentation/fusion line extending in said axial aspect through the series of adjacent vertebral bodies, the anterior axial bore having a caudal axial bore opening through the anterior surface of the sacrum and extending cephalad through at least two vertebral bodies, comprising at least cephalad and caudal vertebral bodies, and any intervening spinal discs;

providing a spinal implant comprising an elongated spinal implant body formed of a bio-compatible material extending between a cephalad spinal implant body end that is dimensioned and configured to be inserted through said caudal axial bore opening and advanced in the cephalad direction to be seated in the cephalad bore end and a caudal spinal implant body portion that is dimensioned and configured to fit within the axial bore traversing the caudal vertebral body; and implanting said elongated spinal implant into said axial bore to extend cephalad and axially through the vertebral bodies of the series of adjacent vertebrae and any intervening spinal discs.

2. The method of claim 1, further comprising the step of engaging at least/a portion of the spinal implant body with vertebral bone exposed by the anterior axial bore to assist in retaining the elongated spinal implant body within the anterior axial bore.

3. The method of claim 2, wherein:

the bone engaging step further comprises the step of providing at least one circumferential, outwardly extending, screw thread extending along at least a portion of the length of the spinal implant body; and the implanting step comprises rotating the elongated spinal implant body to cause the screw thread to bite into the bone of the vertebral bodies surrounding the spinal implant body, the screw thread thereby inhibiting caudal retraction of the spinal implant from the anterior axial bore.

4. The method of claim 2, wherein the bone engaging step further comprises the step of providing an external surface configuration of the spinal implant body that is adapted to engage the vertebral body along at least a portion of the length of the spinal implant body.

5. The method of claim 2, wherein the bone engaging step further comprises the step of providing at least one circumferential, outwardly extending, flange having a leading, in the direction of insertion, conical surface and trailing flange that engages with the bone of the vertebral bodies surrounding a spinal implant body portion through bone ingrowth about the flange within the axial bore and inhibits caudal retraction of the spinal implant from the anterior axial bore.

6. The method of claim 5, wherein the bone engaging step further comprises the step of providing a plurality of said circumferential, outwardly extending flanges spaced apart along the length of the spinal implant body portion.

7. The method of claim 2, wherein the bone engaging step further comprises the step of providing at least one radially and outwardly extending, barb having a leading, in the direction of insertion, tapered surface and a trailing barb tip that bites into the bone of the vertebral bodies surrounding the spinal implant body portion to inhibit caudal retraction of the spinal implant from the anterior axial bore.

8. The method of claim 7, wherein the bone engaging step further comprises the step of providing a plurality of said radially and outwardly extending barbs spaced apart about the spinal implant body.

9. The method of claim 2, wherein the bone engaging step further comprises the step of providing an external surface configuration of the spinal implant body comprising a porous surface formed of a bio-compatible material having pores that accommodate bone growth into the pores to adhere the spinal implant body with vertebral bone to inhibit retraction of the spinal implant body from the anterior axial bore.

10. The method of claim 2, wherein the bone engaging step further comprises the step of providing a plurality of outwardly extending, elongated flutes extending lengthwise along the spinal implant body that bite into the bone of the vertebral bodies surrounding the spinal implant body to inhibit retraction of the spinal implant body from the anterior axial bore.

11. The method of claim 1, wherein the providing step further comprises forming the spinal implant body of a shape memory alloy that possesses a first curvature at a temperature other than body temperature enabling insertion of the spinal implant body into the anterior axial bore in the implanting step and a second curvature within a physiologic body temperature range that applies force to the bone of the vertebral bodies surrounding the spinal implant to inhibit retraction of the spinal implant body from the anterior axial bore to effect fixation to and or re-alignment of the vertebral bodies.

12. The method of claim 11, wherein the providing step further comprises forming an external surface configuration of the spinal implant body that is adapted to engage the vertebral body along at least a portion of the length of the anterior axial bore extending through the series of vertebral bodies upon assumption of the second curvature after advancement of said spinal implant into the anterior axial bore.

13. The method of claim 1, wherein:

the boring step further comprises boring a curved anterior axial bore along a visualized, axial instrumentation/fusion line extending in said axial aspect through the series of adjacent vertebral bodies following the curvature of the spine cephalad from the caudal axial bore opening at the anterior sacral position to the cephalad axial bore end within a lumbar vertebral body;

the providing step further comprises providing the elongated spinal implant having curved spinal implant body that is dimensioned and configured with a curvature that enables insertion into the curved anterior axial bore through said caudal axial bore opening and advancement in the cephalad direction to seat a cephalad spinal implant body portion in the cephalad bore end and to dispose a caudal spinal implant body portion in the axial bore traversing the caudal vertebral body; and the implanting step further comprises the step of aligning the curved spinal implant body with the curvature of the curved anterior axial bore and then inserting the curved spinal implant into the curved anterior axial bore seating the cephalad spinal implant body end within a cephalad end portion of the axial bore traversing a cephalad vertebrae and a caudal spinal implant body portion within a caudal end portion of the curved anterior axial bore traversing a caudal vertebrae.

14. The method of claim 13, wherein the providing step further comprises forming the spinal implant body of a shape memory alloy extending between said cephalad spinal implant body end and said caudal spinal implant body portion that is curved along its length at an implantation temperature that facilitates its insertion in the implanting step into the curved anterior axial bore and that assumes a curvature upon acclimatization of the shape memory material to body temperature that tends to apply force laterally to the vertebral bodies traversed by the axial bore to inhibit retraction of the spinal implant body from the anterior axial bore to effect fixation to and/or re-alignment of the vertebral bodies.

15. The method of claim 14, wherein the providing step further comprises forming an external surface configuration of the spinal implant body that is adapted to engage the vertebral body along at least a portion of the length of the anterior axial bore extending through the series of vertebral bodies upon assumption of the second curvature after advancement of said spinal implant into the anterior axial bore.

16. The method of claim 13, further comprising the step of engaging at least a portion of the spinal implant body with vertebral bone exposed by the anterior axial bore to assist in retaining the elongated spinal implant body within the curved anterior axial bore.

17. The method of claim 16, wherein the engaging step further comprises forming an external surface configuration of the spinal implant body that is adapted to engage the vertebral body along at least a portion of the length of the anterior axial bore extending through the series of vertebral bodies.

* * * * *